US005843736A

United States Patent [19]

Chao

[11] Patent Number: 5,843,736

[45] Date of Patent: Dec. 1, 1998

[54] PREVENTION OF VIRAL INFECTION BY THE INDUCTION OF APOPTOSIS AND/OR THE USE OF AN ANTIVIRAL GENE, HEM1

[75] Inventor: Yu-Chan Chao, Taipei, Taiwan

[73] Assignee: National Science Council of R.O.C., Taiwan

[21] Appl. No.: 249,617

[22] Filed: May 26, 1994

[51] Int. Cl.[6] .............................. C12N 15/00; C12N 5/00

[52] U.S. Cl. .......................... 435/172.3; 435/348; 935/70

[58] Field of Search ................. 514/44, 93.1; 435/172.3, 435/348; 935/70

[56] References Cited

PUBLICATIONS

Clem et al (1993) J. Virol. 67, 3730–3738.
Clem et al (1994) J. Virol. 68, 6759–6762.
Rabizadeh et al (1993) J. Neurochem. 61, 2318–2321.
Bump et al (1995) Science 269, 1885–1888.
Yu et al (1995) Proced. Nat. Acad. Sci. 92, 699–703.
Leavitt et (1994) Human Gene Therapy 5, 1115–1120.
Leib, et al. "A Deletion Mutant of the Latency–Associated Transcript of Herpes Simplex Virus . . .", *Journal of Virology*, pp. 2893–2900, Jul. 1989.
Halstead "Dengue haemorrhagic fever–a public health problem and a field for research", *Bulletin of the WHO*, 59:1–21, 1980.
Halstead "Selective Primary Health Care: Strategies for Control of Disease in the Developing World", *Rev. of Infect. Diseases*, 6,2: 251–264, 1984.
Klein "Are Invertebrates Capable of Anticipatory Immune Responses?", *Scand. J. Immunol.*, 29:499–505, 1989.
Tomei, et al. "Introduction", *Apoptosis: The Molecular Basis of Cell Death*, pp. 1–3, 1991.
Steller, et al. "A transposable P vector that confers electable G418 resistance to Drosophila larvae", *The EMBO Journal*, 4,1: 167–171, 1985.
Kerr, et al. "Definition and Incidence of Apoptosis: An Historical Perspective", *Apoptosis: The Molecular Basis of Cell Death*, pp. 5–29, 1991.
Granados, et al. "An Insect Cell Line Persistently Infected with a Baculovirus–Like Particle", *Intervirology*, 10: 309–317, 1978.
Ralston, et al. "Cell Culture Studies with the IMC–Hz–1 Nonoccluded Virus[1]", *Virology*, 115: 33–44, 1981.
Wood, et al. "Persistent and Productive Infections with the Hz–1 Baculovirus", *Current Topics in Microbiology and Immunology*, 131: 119–133.
Burand, et al. "Persistent Baculovirus Infections", *The Biology of Baculoviruses*, 1: 159–175.
Burand, et al. "Defective Particles from a Persistent Baculovirus Infection in *Trichoplusia ni* Tissue Culture Cells", *Jnl. of Gen. Virology*, 64: 391–398 (1983).
Burand, et al. "Intracellular Protein Synthesis During Standard and Defective Hz–1 Virus Replication", *Jnl. of Gen. Virology*, 67: 167–173.
Huang, et al. "Characterization of the DNA of a Nonoccluded Baculovirus, Hz–1V", *Journal of Virology*, pp. 174–181, Jul., 1982.
Burand, et al. "Structural and Intracellular Proteins of the Nonoccluded Baculovirus Hz–1", *Journal of Virology*, pp. 137–142, Apr., 1983.
Whitaker–Dowling, et al. "Superinfection Exclusion by Vesicular Stomatitis Virus", *Virology*, 131: 137–143, 1983.
Chao, et al. "Physical Map of Hz–1 baculovirus genome from standard and defective interfering particles", *Jnl. of Gen. Virology*, 71: 1265–1270, 1990.
Chao, et al. "Differential Expression of Hz–1 Baculovirus Genes during Productive and Persistent Viral Infection", *Jnl. of Gen. Virology*, pp. 1442–1448, Mar., 1992.
Oldstone "Viral Persistence", *Cell*, 56: 517–520, 1989.
Spivack, et al. "Expression of Herpes Simplex Virus Type 1 Latency–Associated Transcripts in the Trigeminal . . . ", *Journal of Virology*, pp. 1479–1485, May, 1988.
Stevens, et al. "RNA Complementary to a Herpesvirus α Gene mRNA is Prominent in Latently Infected Neurons", *Science Reports*, 2: 1056–1059, 1987.
Vaughn, et al. "The Establishment Of Two Cell Lines From The Insect Spodoptera Frugiperda (Lepodoptera: Noctuidae)", *In Vitro*, 13,4: 213–217, 1977.
Wood "Protease Degradation of *Autographa californica* Nuclear Polyhedrosis Virus proteins", *Virology*, 103: 392–399, 1980.
Clem, et al. "Prevention of Apoptosis by a Baculovirus Gene During Infection of Insect Cells", *Science Reports*, 254: 1388–1390, 1991.
Chen "Flourescent Labeling of Mitochondria", *Methods in Cell Biology*, pp. 103–123, 1989.
Gregory, et al. "Activation of Epstein–Barr virus latent genes protects human B cells from death by apoptosis", *Letters to Nature*, 349: 612–617, 1991.
Wilson "Properties of the Virus Particle", *Classification and Nomenclature of Viruses*, pp. 117–123.
Martz, et al. "CTL: virus control cells first and cytolytic cells second?", *Immunology Today*, 10,3: 79–86, 1989.
Henikoff "Unidirectional digestion with exonuclease III creates targeted breakpoints for DNA sequencing", *Gene*, 28: 351–359, 1984.
Lawler, et al. "The Structure of Human Thrombospondin, an Adhesive Glycoprotein with . . . ", *Jnl. of Cell Biology*, 103: 1635–1648, 1986.
Sanger, et al. "DNA sequencing with chain–terminating inhibitors", *Proc. Natl. Acad. Sci.*, 74,12: 5463–5467, 1977.
Chen, et al. "Supercoil Sequencing: A Fast and Simple Method for Sequencing Plasmid DNA", *DNA*, 4,2: 165–170, 1985.

(List continued on next page.)

*Primary Examiner*—Deborah Crouch
*Attorney, Agent, or Firm*—Foley & Lardner

[57] ABSTRACT

Disclosed is a new, effective and general methodology to prevent viral infection, which methodology is divided into two parts: 1) induction of the apoptosis (programmed cell death) of a host upon viral infection to block viral reproduction; and 2) the use of an apoptosis triggering gene, the persistency-associated gene 1 (pag1, now renamed as hem1 in light of the position thereof in the restriction map of the Hz-1 viral genome) to prevent the viral infection.

4 Claims, 22 Drawing Sheets

OTHER PUBLICATIONS

Tabor, et al. "DNA sequence analysis with a modified bacteriophage T7 DNA polymerase", *Proc. Natl. Acad. Sci.*, 84: 4767–4771, 1987.

Chao, et al. "Investigate The Nature Of Viral Persistent Infections Using Hz–1 Baculovirus As A Model System", *Mol. Ent. Symp.*, pp. 33–47, Jul., 1990.

Aubusel, et al. "Preparation and Analysis of RNA", *Current Protocols In Molecular Biology*pp. 4.0.1–4.2.2, 1988.

Stephenson, et al. "Molecular analysis of the swallow gene on *Drosophila melanogaster", Genes and Development*, 2: 1655–1665, 1988.

Melton, et al. "Efficient in vitro synthesis of biologically active RNA and RNA . . . ", *Nucleic Acids Research*, 12, 18: 7035–7056, 1984.

Fickett "Recognition of protein coding regions in DNA sequences", *Nucleic Acids Research*, 10,17: 5303–5318, 1982.

Zuker, et al. "Optimal computer folding of large RNA sequences using thermodynamics and auxiliary information", *Nucleic Acids Research*, 9,1: 133–148, 1981.

Freier, et al. "Improved free–energy parameters for predictions of RNA duplex stability", *Proc. Natl. Acad. Sci.*, 83: 9373–9377, 1986.

Spivack, et al. "Detection of Herpes Simplex Virus Type 1 Transcripts during Latent Infection in Mice", *Journal of Virology*, pp. 3841–3847, Dec., 1987.

Steiner, et al. "Herpes simplex virus type 1 latency–associated transcripts re evidently not essential . . . ", *The EMBO Journal*, 8,2: 505–511, 1989.

Ho, et al. "Herpes simplex virus latent RNA (LAT) is not required for latent infection in the mouse", *Proc. Natl. Acad. Sci.*, 86: 7596–7600, 1989.

Block, et al. "A Herpes Simplex Virus Type 1 Latency–Associated Transcript Mutant Reactivates . . . ", *Journal of Virology*, pp. 3417–3426, Jul., 1990.

Zwaagstra, et al. "Activity of Herpes Simplex Virus Type 1 Latency–Associated Transcript (LAT) Promoter in Neuron––Derived Cells . . .", *Journal of Virology*, pp. 5019–5028, Oct., 1990.

Sharp, et al. "HIV TAR: An RNA Enhancer?", *Cell*, 5–: 229–230, 1989.

Brockdorff, et al. The Product of the Mouse Xist Gene Is a 17 kb Inactive X–Specific Transcript Containing . . . , 71: 515–526, 1992.

Brown, et al. "The Human Xist Gene: Analysis of a 17 kb Inactive X–Specific RNA That Contains . . . ", *Call*, 71: 527–542, 1992.

Lee, et al. "Pulse–Labeled Ribonucleic Acid Complexes Released by Dissociation of Rat Liver Polysomes", *Biochemistry*, 10,3: 510–517, 1971.

Brockdorff, et al. "Conservation of position and exclusive expression of mouse Xist from the inactive X chromosome", *Letters to Nature*, 351: 329–331, 1991.

Brown, et al. "A gene from the region of the human X inactivation centre is expressed exclusively from . . . ", *Nature*, 349: 38–44, 1991.

Campbell, et al. "Identification of Herpes Simplex Virus DNA Sequences Which Encode a Trans–acting Polypeptide . . . ", *J. Mol. Biol.*, 180: 1–19, 1984.

Steiner, et al. "A Herpes Simplex Virus Type 1 Mutant Containing a Nontransinducing Vmw65 Protein . . . ", *Journal of Virology*, pp. 1630–1638, Apr., 1990.

Weinheimer, et al. "Deletion of the VP16 Open Reading Frame of Herpes Simplex Virus Type 1", *Journal of Virology*, pp. 258–269, Jan., 1992.

Rooney, et al. "Genome rearrangements activate the Epstein–Barr virus gene whose product disrupts latency", *Proc. Natl. Acad. Sci.*, 85: 9801–9805, 1988.

Flemington, et al. "Autoregulation of Epstein–Barr Virus Putative Lytic Switch Gene BZLF1", *Journal of Virology*, pp. 1227–1232, Mar., 1990.

Sinclair, et al. "Reciprocal Antagonism of Steroid Hormones and BZLF1 in Switch between Epstein–Barr . . . ", *Journal of Virology*, pp. 70–77, Jan., 1992.

Kay, et al. "Expression of Xist during Mouse Development Suggests a Role in the Initiation of X Chromosome Inactivation", *Cell*, 2: 171–182, 1993.

Lee, et al. "Superinfection–Induced Apoptosis and Its Correlation with the Reduction of Viral . . . ", *Journal of Virology*, pp. 6989–6994, Dec., 1993.

FIG. 5B-1

```
1     GGTACCAGAC TATGGTGCCA GACTTTCAGA CATCATCTTT CCAGACTTTA
101   CATATTCAAA TTATTCTATT CATCCTCTCT CAACATCACC CCTCGTAGAC
201   ATTAAATATT AAACAATTGT AATTTAGTAT TAAATAATTT AGTATTGAAC
301   CAAAATTGAA AATTGACACA GTTACCCCTC GCGCAGAGTC CCGGCTATGC
401   TCTTGATTTG CATCTGAATT GGTATAACCT CGATTGTAAA CAATGAACTG
501   AAGCGTTTGT TTATAGCTTT ATACGTTGAA GATACATTCA AAATTCATTC
601   CAACAGACCC TCGGGACCGG TATAATTGTA GGCGTTTAAT TATTGTTATA
701   CTAGACAACG CCAGAGACGG GACAGATGCA TTGGATGCAT CAAAAGTGTA
801   TTTTAGGACA AACCAGAGTA CAGAGACACC ACATGTGAGG TATCCCACAG
901   AAGAATCATT AAGAGGAATC GTTCCCCCCG CAGAAGAATC TAGTAGGTGT

1001  GGTTCTTATC GCAACAGAGT GGGGGCCATC CGCACTATAA AAAGCCGAGA
1101  GTGTAGGCAG CGTCTGGTAC TAGGTGAGTG GCTCATTCTT ATTTAATTCA
1201  CATCTGATAC ACTTTTTATA GCTCTTAGCA TACTTAAATT TTATGGAGCG
1301  CTCTTTGCCA AAACCAAACA CAACTCGCAT CTGATCCGCT CTGTGTTCGA
1401  CACAAGCCAC TGCTCCTATG CAAACGGGTT CCTTTGGTTC GATTGTGTCG
1501  GGGAGTAGGT AGCATAGATG ACTCGGGCTG TCGCTTAACG TTGAATACGC
1601  CATACTGGTA CCCGTTTTGG CACTGTAGTA TCGGCAACGG TAATGCAGTG
1701  CTCGTTTATG AATAATGTTA TTATTCTACA TTAGTCTTAT CTGGCCCGGC
1801  TAATAACAAT GGTAATGTGT GCGTGTCGGG CATCTATAAA TACACGTGTG
1901  ACCATAGGGA CTTTTAGTTT TGTTAGTGTA GTGTTTTTGA GTGCAAGATG
2001  GAACAGTACT ACTACTAGAG GATAGCGTTT AGTAGAGGTG CTGGGAACAA
2101  TGCTTTTACA TTTTATGGTT CATTACTTGA CACTGATTGA TATTTTATAC
2201  GAATCTAGGT AGGTAGGGTT TTACACATGC TTACACATAC ACACTGACAC
2301  AAACGGAAAA CCAATACCAT ACATTCTATC ATTCTATCCT TCTACTATTA
2401  ACACACATGG ATTTGTGCTC ACAACAACAA AACACAATCG GTTAGGGTCG
2501  TTAGTCTGTA AGCGGTACGG CTAGTTTATA AGGCTCGGTT AGTTATAAGG
2601  TTTATAAGTC CGGTTAGATT TAAGTGCGGC TAGTGTATAA GTCGGTGTGA
2701  AAATTGATAC ACGACGGTAA ACAAGAGTTG ATTTGTGTAG TATACGTCTT
2801  TAAAAACACG GGTTGTACAC ATTTACACAT ACACACTATA CACACCAATT
2901  TAAAGACTGG TGGTAAGACT GGCATATACT GGTATATAAA TGCAAGGATA
3001  CTTTGTGTAC TCTGGTACTC TGATAAAGCT ATACTCTGGT AAATACTCTG
3101  ACAACAACAA ATCTGGTAAC TCGGTGACTC TGACTCTGGC GTCTCTTGGT
3201  AAAGGTATTG GTATCAAATA ACGGTATCAA AGGTATTACA CAAAGGTATT
3301  ACACACATAA GTTAAGCACA CGTAGTAAAT GCACAGTACG TAGGGTGTCT
3401  GCGTAGAGTC AAACCTTTGG CATGGTTTGT ATCGCATGCA ACACCAAAGC
3501  CCATCCCCAT ACAAGAGTTC ACTAACCATA CTCTAAATGG TATCGTATTG
3601  AGCAAAAGTC TTGCACACCT AGGCGTGCGA TGCGATCGTT AGGCTCTGTG
3701  CACGTTGTCT TTCAGGCAGT CTCTCGTGGC GTGTGCGCTT GTTTGCTTTG
3801  AGTTGTGGAC ATATGCGATC GATTGCCTCG CAGTAATCGG CTACGATAAC
3901  ACGCTCTTGC CAATTAACGT TAACGTAGAG TCAGTATTTT AATATTAAAA

4001  ACATTTGTTG TTTCATTTTA TACATCCTGC ATCCTGATAC AACCTTTACA
4101  TTAGGTAGAC TGTACTGTAG GCTGTTGTTG TGTGTTAGGT TTGATACAAA
4201  CTATTATAGA GTTGTGATTG AGTATAGAGT TACTTTTTGA AGAGTATTGG
```

FIG. 5B-2

CTCATTCAAA TCATCTTTAT ACATTCACAT TCAAATCATC TCTCTACATC
CTAAGTTTTC ATCACGTCTA CTTTTAAAAT AAACACGGAC TATACTTGTA
AATCTCTATA TACATAATCG TCTACATTTG AGGTTATAAA ACGTTGTATG
GCAAGAGTGT AGTTTAAAGT GTCTGGCTAC ATTTTAGCAT CAGTCAAATG
GGTGTGCACG TCGCCATCTT GTTGTGTTAA TTTATTATGC ATGTTAATTT
ACACGGTTAG AATAACGGTA TTGGAATCTA GAAACTAGAC CTTTAGGTCG
AAAGGGTAGT ATTTAATGTT GTAGCGAGCC GTCCAATGAC TGGCTATAGA
AAATTTAAAG AGCTAGCGGT AAAAATGATA AAAGTATAC AAATGTACAC
ATGGTCTTGT GAAAAGGAGT CCAAAAATGT AAAAAAGAAT AATCATGTAG
GCACGTTTTT CTGATAAAGT TTTATTACTC ATCGACCAAT GGCGTCGCTC

+1

CTGGTGACGA ACACCATCAG TCTGATTCGA GTCGTGTTCA TACCGCACTG
TTTAATTTGT CTGCTCTGTT TATTCAATTT TAAAATGTGC AGTCTCGGGT
GAGTAATCGA CCCGAATCGG ACCTCGGTCT GGTACGAAAC GATAGCACTG
GACATGTTGT CCGAATGTGT TCCTTAAAGG CGACATGCGA CCTTGTTGGT
CACGAGTGGA TGCTAAATTC GCGTGCAGGT GTCGAGACTT AGACTTTTTA
AGGGTGGACT CTTTGAATGG ATTTTATTCA GATGCCACCT CGACTCGAAT
TCGAGACTTA AACTCTTGGT GGCACAGTGT ATAAACTGTA GGTTCTCTCT
ATGTACTAGG TAGGATGTTT TTATTATATA CACACATGTG CATTTGAGGA
CGTGTGTGCT GTTTTATTAT TATTAGGTAG GCGTAGCTTG CACATGTGCC
TTTGTTTTTA CTGTGCATTT ACAAGAGACT TGATGGAACA CTTATATGTA
TAGTGTGCCG AGTATAATCA TAGGTATGTG TTGCAATACT TTTTATTTTA
TTGTTGATAT TGTGTGGATA ATTTATGAGA TAATTTATGA CCATCTGTGG
TGACACACAT TTTACAAACC AAACCAAACA AAACAAAAGT ACATTAAAAC
CTACCACTAT CTACTATGGG TACCTACCAA ACATTTTTAA ATCTATACAT
TTGGGTCTGT TGCAGTCTCG GCAGCTTAGG TCGGTTAGTT TTAGGCTCGG
TAGGCTCGGT TAGATATAAG GTTCGGTTAG CTATAAGTCG GTGCGGCTAG
GCACAAATCA ATAGATGTAG TAAGATGTGA TACTTTATGA ATTGAATTAT
CTTCTTCCTA CTTCCTACTA TTGCAAACAA TATAAAAAAA ACATATAAAA
TAGGGTTACG ATAATTTAGG ACATTTAGGA TAATGACAAA GTGTCTCTGG
CAACTAGGTA CGGTACTCTG CAACTACTAT ACTCTGGTAT ACTCGGCAAA
GTAGAACTCT GTACTCTGAT ATACTCTGGT ACTTTTGTAC ATATACAACT
AACTCTGGTG GTATTGGTAT TGGTTAATAA AGGTATCAAC GGTTTCAAAC
AAACAAAGGT ATTAAACAAA AGGTATCAAA CAATAGGTTT AGGCAAATGC
AGTGCAGAAT TTGATACTAT GAGCGTTTCG GTTCGGTACC GTTTAAGAGG
TAGTGGTGCA TGTTATGCTC TCCGTGCCTC ATATCCCAAT AATAACCAAC
AAAGAGTTTG TTGTATTCAA TTCTTGCACA ATTCGTGTAG ATTAGAATGC
TACGAGTATC GCATTGCACA ACAACCCACT GACCAACCCC CTCGCACCGT
CAAAGAGATT GCCTTAGTGC CTTGTTGCAA CCGTGGCGTG CAAGTGTTTG
GCTGCCTGGT ATCTCCGATG TACATTGTCG TTAACACACA AAAAACGTGC
CGGTTTTTTT CTTTTTTTTT CACCACCCAA TAAACTAACA ATTACTGGTG

CGAACTGCTG TTAGGTAGAG TGTTTTATTA GGTAGAGTGT TTTGTTACAG
CATACAAATA TACAAATACA TAAAACCAGA GTTACCACTA GGGTTTGAGA
TATTCTGAAG AGTATTGGTA TTCTACAAGT ATCCTG

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4286 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

-continued

| | | | | | | |
|---|---|---|---|---|---|---|
| GGTACCAGAC | TATGGTGCCA | GACTTTCAGA | CATCATCTTT | CCAGACTTTA | CTCATTCAAA | 60 |
| TCATCTTTAT | ACATTCACAT | TCAAATCATC | TCTCTACATC | CATATTCAAA | TTATTCTATT | 120 |
| CATCCTCTCT | CAACATCACC | CCTCGTAGAC | CTAAGTTTTC | ATCACGTCTA | CTTTTAAAAT | 180 |
| AAACACGGAC | TATACTTGTA | ATTAAATATT | AAACAATTGT | AATTTAGTAT | TAAATAATTT | 240 |
| AGTATTGAAC | AATCTCTATA | TACATAATCG | TCTACATTTG | AGGTTATAAA | ACGTTGTATG | 300 |
| CAAAATTGAA | AATTGACACA | GTTACCCCTC | GCGCAGAGTC | CCGGCTATGC | GCAAGAGTGT | 360 |
| AGTTTAAAGT | GTCTGGCTAC | ATTTTAGCAT | CAGTCAAAGT | TCTTGATTTG | CATCTGAATT | 420 |
| GGTATAACCT | CGATTGTAAA | CAATGAACTG | GGTGTGCACG | TCGCCATCTT | GTTGTGTTAA | 480 |
| TTTATTATGC | ATGTTAATTT | AAGCGTTTGT | TTATAGCTTT | ATACGTTGAA | GATACATTCA | 540 |
| AAATTCATTC | ACACGGTTAG | AATAACGGTA | TTGGAATCTA | GAAACTAGAC | CTTTAGGTCG | 600 |
| CAACAGACCC | TCGGGACCGG | TATAATTGTA | GGCGTTTAAT | TATTGTTATA | AAAGGGTAGT | 660 |
| ATTTAATGTT | GTAGCGAGCC | GTCCAATGAC | TGGCTATAGA | CTAGACAACG | CCAGAGACGG | 720 |
| GACAGATGCA | TTGGATGCAT | CAAAAGTGTA | AAATTTAAAG | AGCTAGCGGT | AAAAATGATA | 780 |
| AAAAGTATAC | AAATGTACAC | TTTTAGGACA | AACCAGAGTA | CAGAGACACC | ACATGTGAGG | 840 |
| TATCCCACAG | ATGGTCTTGT | GAAAAGGAGT | CCAAAAATGT | AAAAAAGAAT | AATCATGTAG | 900 |
| AAGAATCATT | AAGAGGAATC | GTTCCCCCCG | CAGAAGAATC | TAGTAGGTGT | GCACGTTTTT | 960 |
| CTGATAAAGT | TTTATTACTC | ATCGACCAAT | GGCGTCGCTC | GGTTCTTATC | GCAACAGAGT | 1020 |
| GGGGGCCATC | CGCACTATAA | AAAGCCGAGA | CTGGTGACGA | ACACCATCAG | TCTGATTCGA | 1080 |
| GTCGTGTTCA | TACCGCACTG | GTGTAGGCAG | CGTCTGGTAC | TAGGTGAGTG | GCTCATTCTT | 1140 |
| ATTTAATTCA | TTTAATTTGT | CTGCTCTGTT | TATTCAATTT | TAAAATGTGC | AGTCTCGGGT | 1200 |
| CATCTGATAC | ACTTTTTATA | GCTCTTAGCA | TACTTAAATT | TTATGGAGCG | GAGTAATCGA | 1260 |
| CCCGAATCGG | ACCTCGGTCT | GGTACGAAAC | GATAGCACTG | CTCTTTGCCA | AAACCAAACA | 1320 |
| CAACTCGCAT | CTGATCCGCT | CTGTGTTCGA | GACATGTTGT | CCGAATGTGT | TCCTTAAAGG | 1380 |
| CGACATGCGA | CCTTGTTGGT | CACAAGCCAC | TGCTCCTATG | CAAACGGGTT | CCTTTGGTTC | 1440 |
| GATTGTGTCG | CACGAGTGGA | TGCTAAATTC | GCGTGCAGGT | GTCGAGACTT | AGACTTTTTA | 1500 |
| GGGAGTAGGT | AGCATAGATG | ACTCGGGCTG | TCGCTTAACG | TTGAATACGC | AGGGTGGACT | 1560 |
| CTTTGAATGG | ATTTTATTCA | GATGCCACCT | CGACTCGAAT | CATACTGGTA | CCCGTTTTGG | 1620 |
| CACTGTAGTA | TCGGCAACGG | TAATGCAGTG | TCGAGACTTA | AACTCTTGGT | GGCACAGTGT | 1680 |
| ATAAACTGTA | GGTTCTCTCT | CTCGTTTATG | AATAATGTTA | TTATTCTACA | TTAGTCTTAT | 1740 |
| CTGGCCCGGC | ATGTACTAGG | TAGGATGTTT | TTATTATATA | CACACATGTG | CATTTGAGGA | 1800 |
| TAATAACAAT | GGTAATGTGT | GCGTGTCGGG | CATCTATAAA | TACACGTGTG | CGTGTGTGCT | 1860 |
| GTTTTATTAT | TATTAGGTAG | GCGTAGCTTG | CACATGTGCC | ACCATAGGGA | CTTTTAGTTT | 1920 |
| TGTTAGTGTA | GTGTTTTTGA | GTGCAAGATG | TTTGTTTTTA | CTGTGCATTT | ACAAGAGACT | 1980 |
| TGATGGAACA | CTTATATGTA | GAACAGTACT | ACTACTAGAG | GATAGCGTTT | AGTAGAGGTG | 2040 |
| CTGGGAACAA | TAGTGTGCCG | AGTATAATCA | TAGGTATGTG | TTGCAATACT | TTTTATTTTA | 2100 |
| TGCTTTTACA | TTTTATGGTT | CATTACTTGA | CACTGATTGA | TATTTTATAC | TTGTTGATAT | 2160 |
| TGTGTGGATA | ATTTATGAGA | TAATTTATGA | CCATCTGTGG | GAATCTAGGT | AGGTAGGGTT | 2220 |
| TTACACATGC | TTACACATAC | ACACTGACAC | TGACACACAT | TTTACAAACC | AAACCAAACA | 2280 |
| AAACAAAAGT | ACATTAAAAC | AAACGGAAAA | CCAATACCAT | ACATTCTATC | ATTCTATCCT | 2340 |
| TCTACTATTA | CTACCACTAT | CTACTATGGG | TACCTACCAA | ACATTTTTAA | ATCTATACAT | 2400 |

-continued

| | | | | | | |
|---|---|---|---|---|---|---|
| ACACACATGG | ATTTGTGCTC | ACAACAACAA | AACACAATCG | GTTAGGGTCG | TTGGGTCTGT | 2460 |
| TGCAGTCTCG | GCAGCTTAGG | TCGGTTAGTT | TTAGGCTCGG | TTAGTCTGTA | AGCGGTACGG | 2520 |
| CTAGTTTATA | AGGCTCGGTT | AGTTATAAGG | TAGGCTCGGT | TAGATATAAG | GTTCGGTTAG | 2580 |
| CTATAAGTCG | GTGCGGCTAG | TTTATAAGTC | CGGTTAGATT | TAAGTGCGGC | TAGTGTATAA | 2640 |
| GTCGGTGTGA | GCACAAATCA | ATAGATGTAG | TAAGATGTGA | TACTTTATGA | ATTGAATTAT | 2700 |
| AAATTGATAC | ACGACGGTAA | ACAAGAGTTG | ATTTGTGTAG | TATACGTCTT | CTTCTTCCTA | 2760 |
| CTTCCTACTA | TTGCAAACAA | TATAAAAAAA | ACATATAAAA | TAAAAACACG | GGTTGTACAC | 2820 |
| ATTTACACAT | ACACACTATA | CACACCAATT | TAGGGTTACG | ATAATTTAGG | ACATTTAGGA | 2880 |
| TAATGACAAA | GTGTCTCTGG | TAAAGACTGG | TGGTAAGACT | GGCATATACT | GGTATATAAA | 2940 |
| TGCAAGGATA | CAACTAGGTA | CGGTACTCTG | CAACTACTAT | ACTCTGGTAT | ACTCGGCAAA | 3000 |
| CTTTGTGTAC | TCTGGTACTC | TGATAAAGCT | ATACTCTGGT | AAATACTCTG | GTAGAACTCT | 3060 |
| GTACTCTGAT | ATACTCTGGT | ACTTTTGTAC | ATATACAACT | ACAACAACAA | ATCTGGTAAC | 3120 |
| TCGGTGACTC | TGACTCTGGC | GTCTCTTGGT | AACTCTGGTG | GTATTGGTAT | TGGTTAATAA | 3180 |
| AGGTATCAAC | GGTTTCAAAC | AAAGGTATTG | GTATCAAATA | ACGGTATCAA | AGGTATTACA | 3240 |
| CAAAGGTATT | AAACAAAGGT | ATTAAACAAA | AGGTATCAAA | CAATAGGTTT | AGGCAAATGC | 3300 |
| ACACACATAA | GTTAAGCACA | CGTAGTAAAT | GCACAGTACG | TAGGGTGTCT | AGTGCAGAAT | 3360 |
| TTGATACTAT | GAGCGTTTCG | GTTCGGTACC | GTTTAAGAGG | GCGTAGAGTC | AAACCTTTGG | 3420 |
| CATGGTTTGT | ATCGCATGCA | ACACCAAAGC | TAGTGGTGCA | TGTTATGCTC | TCCGTGCCTC | 3480 |
| ATATCCCAAT | AATAACCAAC | CCATCCCCAT | ACAAGAGTTC | ACTAACCATA | CTCTAAATGG | 3540 |
| TATCGTATTG | AAAGAGTTTG | TTGTATTCAA | TTCTTGCACA | ATTCGTGTAG | ATTAGAATGC | 3600 |
| AGCAAAAGTC | TTGCACACCT | AGGCGTGCGA | TGCGATCGTT | AGGCTCTGTG | TACGAGTATC | 3660 |
| GCATTGCACA | ACAACCCACT | GACCAACCCC | CTCGCACCGT | CACGTTGTCT | TTCAGGCAGT | 3720 |
| CTCTCGTGGC | GTGTGCGCTT | GTTTGCTTTG | CAAAGAGATT | GCCTTAGTGC | CTTGTTGCAA | 3780 |
| CCGTGGCGTG | CAAGTGTTTG | AGTTGTGGAC | ATATGCGATC | GATTGCCTCG | CAGTAATCGG | 3840 |
| CTACGATAAC | GCTGCCTGGT | ATCTCCGATG | TACATTGTCG | TTAACACACA | AAAAACGTGC | 3900 |
| ACGCTCTTGC | CAATTAACGT | TAACGTAGAG | TCAGTATTTT | AATATTAAAA | CGGTTTTTTT | 3960 |
| CTTTTTTTTT | CACCACCCAA | TAAACTAACA | ATTACTGGTG | ACATTTGTTG | TTTCATTTTA | 4020 |
| TACATCCTGC | ATCCTGATAC | AACCTTTACA | CGAACTGCTG | TTAGGTAGAG | TGTTTTATTA | 4080 |
| GGTAGAGTGT | TTTGTTACAG | TTAGGTAGAC | TGTACTGTAG | GCTGTTGTTG | TGTGTTAGGT | 4140 |
| TTGATACAAA | CATACAAATA | TACAAATACA | TAAAACCAGA | GTTACCACTA | GGGTTTGAGA | 4200 |
| CTATTATAGA | GTTGTGATTG | AGTATAGAGT | TACTTTTTGA | AGAGTATTGG | TATTCTGAAG | 4260 |
| AGTATTGGTA | TTCTACAAGT | ATCCTG | | | | 4286 |

( 2 ) INFORMATION FOR SEQ ID NO:2:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i v ) ANTI-SENSE: YES ( x i ) SEQUENCE DESCRIPTION: SEQ ID NO:2:

AATAAGAATG AGCCACTCAC CTAGTACCAG ACGCT 35

PREVENTION OF VIRAL INFECTION BY THE INDUCTION OF APOPTOSIS AND/OR THE USE OF AN ANTIVIRAL GENE, HEM1

Disclosed is a new, effective and general methodology to prevent viral infection, which methodology is divided into two parts: 1) induction of the apoptosis of a host upon viral infection to block viral reproduction; and 2) the use of an apoptosis triggering gene, the persistency-associated gene 1 (pag1, now renamed as hem1 in accordance with the position thereof in the restriction map of the Hz-1 viral genome) to prevent the viral infection.

BACKGROUND OF THE INVENTION

Viral infections have nowadays become a severe and urgent medical problem worldwide. Insofar as the human being and other vertebral animals are concerned, almost all the diseases caused by viruses can only be treated by prevention. That is, the most commonly used method to prevent viral infection to date is the immunization of an animal. So far, however, it appears that many viral diseases, such as the Dengue fever, that can not be effectively prevented by a vaccine. Further, in the case of viral diseases that could be effectively treated by prevention, it is still difficult to combat such viruses if the target hosts thereof were infected prior to prevention and then developed to a state of latent infection. Besides, although vertebrates can be immunized with a vaccine and usually give rise to good results in preventing viral infection, there are some serious problems in using this approach.

Firstly, vaccines are not available to all the viruses for the general public. For instance, vaccines for immunizing against human immunodeficiency virus (HIV) and hepatitis C virus (HCV) have yet to be available to the general public. Also, different vaccines must be used for different viruses and not every antigen derived from a virus is effective in the fight against the same virus. Secondly, in some cases, viral infection can be accelerated by the pre-existence of the antibody in the infected subject. The Dengue virus is an example (S. B. Halstead, *Bulletin of the World Health Organization*, 59: 1–21, 1980; and *Review of Infectious Diseases*, 6: 251–264, 1984). In such cases, vaccination can result in an even worse consequence.

To most animals other than the vertebrates, such as silkworms, honey bees, shrimps and so on, which do not at all develop an antibody generation system and thus are unable to elicit the formation of an immune anti-serum (J. Klein, *Scand. J. Immunol*., 29: 499–505, 1989), the conventional vaccination therapy will have no effect thereupon; even though the therapy might work, it still appears impractical to vaccinate said animals by virtue of the tiny bodies thereof. Therefore, it is desirable to develop a more effective and efficient approach to render such subjects to become antiviral. To this end, genetic engineering appears to open an entirely new and promising field for investigation and development.

Heretofore, no investigation upon animal disease prevention by means of gene modification has been reported. This might be due to the lack of available antiviral genes for use.

SUMMARY OF THE INVENTION

In order to combat the above-outlined problems, the present inventor has developed a completely new method to prevent viral infection. This method is the induction of early apoptosis (programmed cell death) upon viral infection of a particular cell. The apoptosis which results in cell death is induced before viral maturation and, therefore, the virus will be killed in such cells. Subsequently, the inventor found that a virus encodes a gene named the persistency-associated gene 1 (pag1, now renamed as hem1 in accordance with the position thereof in the restriction map of the Hz-1 viral genome), and this gene induces apoptosis upon viral infection and results in viral homologous and heterologous interference.

To be specific, it has been recently discovered from the inventor's research aimming at the antiviral phenomenon of insect cells, Which were persistently infected with baculovirus (HZ-1 virus), that the viral persistency-associated gene hem1 in itself is the gene responsible for the antiviral phenomenon. Said phenomenon and said gene per se have the following characteristics:

1) that persistently infected cells are resistant to viral infection is a ubiquitous biological phenomenon; however, hem1 is the first gene which was found to have antiviral effects by way of triggering the emergence of apoptosis;
2) apoptosis is a conserved phenomenon existing amongst almost all organisms and it acts in a substantially identical manner from nematodes through insects to humans (L. D. Tomi and D. C. Frederick (1991), *Apoptosis: The molecular basis of cell death*, Cold Spring Harbour Laboratory Press); therefore, it would be feasible to induce apoptosis in a variety of organisms to achieve the desired antiviral effect; and
3) the antiviral phenomenon observed in baculovirus persistent infection appears to be an outcome of the long-term natural evolution and, as a consequence, the antiviral activity of the hem1 gene will not be easily overwhelmed by a virus; that is, its antiviral activity would be more thoroughly effective and last a longer time than those derived from traditional medicament therapy.

In light of the aforesaid, it is comprehensible that both the induction of apoptosis in a cell and the activity of the hem1 gene have a broad spectrum against viral infection; a new methodology for the treatment of viral infections by such mannner is then promising.

This invention therefore relates to the use of apoptosis stimulants to trigger and/or enhance apoptosis upon viral infection. These stimulants make the cells become very sensitive to the infection of virus. Upon the infection of the virus to these sensitized cells, early apoptosis is induced which results in a significant decrease of the progeny virus. Viral resistance is thus achieved. There are two ways to establish viral resistance in accordance with this invention:

I. An apoptosis stimulant can be the virus itself. The simple introduction of the virus into the cell can achieve such result. In order to do this, the first step is to establish a viral persistent infection in the host cell. The persistently infecting virus thus becomes an efficient apoptosis stimulant.

This is proved by using the Hz-1 baculovirus and SF9 cells (insect cell line derived from *Spodoptera frugiperda*, the fall armyworm), in which SF9 cells were infected with Hz-1 at a multiplicity of infection (m.o.i.) of 10; ten days later, cell colonies which were persistently infected with the Hz-1 baculovirus were established and exhibited strong homologous interference upon Hz-1 baculovirus infection; the cell colonies thus constructed were resistant not only to the homologous virus, but also to other viruses and exhibited heterologous interference, if that virus did not have a gene to block apoptosis; the latter was evidenced by challenging the persistently infected cell with the p35 minus AcMNPV virus (the apoptosis blocking gene, p35 gene, was removed from Autographa california multiple nuclear polyhedrosis virus, AcMNPV).

II. The hem1 gene functions as an apoptosis stimulant. hem1 was taken from the EcoRI-M fragment of the Hz-1 viral genome, ligated with a neomycin resistant gene, and transfected into the cell; resistant clones were screened by antibiotic G418 (Sigma Co., USA); and intense apoptosis was triggered upon challenge of Hz-1 baculovirus to these hem1 gene inserted cell clones.

Features and advantages of the present invention will become apparent in the following detailed description of the preferred embodiments, with reference to the accompanying drawings, of which:

BRIEF DESCRIPTION OF THE DRAWINGS

FIG. 1A. Rhodamine 123-stained SF9 and SFP1 cells at 17 hours, postinfection (h.p.i.) (SF9-17h.a and SFP1-17h.a) and bright-field picture of SF9 and SFP1 cells at 17 h.p.i. (SF9-17h.b and SFP1-17h.b). Panels SF9-17h.a and SF9-17h.b show the same field; similarly, SFP1-17h.a and SFP1-17h.b show the same field. Necrotic cells were not stainable with rhodamine 123, as indicated by arrows (SF9-17h.a and SF9-17h.b); apoptotic cells and apoptotic bodies could be stained since they contained intact mitochondria, and are indicated by large and small arrowheads respectively (SFP1-17h.a and SFP1-17h.b). FIG. 1B. Bright field pictures of SF9, SFP1 and SFP2 cells were taken separately at 17, 36 and 96 h.p.i.;

FIG. 4A Panels: 1 and 2, mock-infected SF9 cells; 3 and 4, Hz-1 baculovirus-infected SF9 cells; 5 and 6, Hz-1 baculovirus-infected SFP1 cells. Panels 1, 3 and 5: bright-field images of infected cells; panels 2, 4 and 6: fluorescent images of infected cells. The large arrows indicate necrotic SF9 cells (panels 3 and 4). The small arrows indicate necrotic or nonapoptotic SFP1 cells which were stainable by the fluorescent antibody (panels 5 and 6). The arrowheads indicate apoptotic SFP1 cells which were not stainable by the fluorescent antibody (panels 5 and 6). FIG. 4B Vertical bars showing percentages of antibody-stained necrotic (N), healthy-looking (H) , and apoptotic cells. Filled bars indicate percentages of unstained cells and hatched bars indicate stained cells;

FIGS. 5A, 5B and 5C. Restriction map, sequence of hem1, and primer extension strategies. FIG. 5A The hem1 gene and the lateral sequences are contained in the plasmid pHzE-M. The viral insert of this plasmid includes the viral EcoRI-M fragment and an adjacent 0.3 kb EcoRI-HindIII fragment. The region sequenced is denoted by a bold line. The PAT1 and its orientation are shown by the large arrow. (FIG. 5B-1 and FIG. 5B-2) The nucleotide sequence of hem1 (SEQ ID NO:1). Putative GATA motif and CAAT and TATA boxes are underlined. The transcription start site is indicated by an arrow and the transcription termination site is indicated by a star. FIG. 5C Primer extension experiments using the total RNA extracted from the persistently infected cell line TNPC3. Lanes 1–4 are sequence ladders; extended (78 bp) or primer (35 bp) bands derived from the total RNAs which were extracted from viral persistently infected TNPC3 (lane 5) and parental TN368 (lane 6) cells are shown;

FIG. 6A ORF analysis of hem1 and adjacent regions. ORFs are indicated as open boxes. Start codons are marked with upper bars and stop codons are marked with lower bars. The orientations of the top three reading frames are the same as the PAT1. The orientations of the bottom three reading frames are opposite from the PAT1. The region encoding PAT1 is indicated by an arrow. FIG. 6B Testcode analysis of PAT1 encoding region. Testcode is a computer program used to identify protein coding sequences by plotting a measure of the non-randomness of the composition at every third base. The top region is supposed to predict coding regions to a 95% level of confidence. The bottom region is supposed to predict non-coding regions to the same confidence level. The middle region is the zone where the statistic can make no significant prediction;

FIG. 7A direct FIG. 7B inverted repeats are indicated on both ends of every line. Only those repeats larger than 10 bases are shown;

FIG. 8A Strategies to insert a Drosophila heat shock promoter driven neomycin resistant gene to the plasmid pHzE-M. The hsp/neo gene was excised from cosmid cosPneo (Steller and Pirrota, *EMBO J.*, 4:167–171, 1985) using the restriction enzyme HindIII. This gene was inserted into plasmid pHzE-M using the unique HindIII. site. The resulting plasmid pPAG-N was linearized using ClaI and transfected into the TN363 cell line. FIG. 8B Southern hybridization showed that the plasmid pPAG-N was inserted in the host genomes. Purified pPAG-N DNA and genomic DNAs from all eight transformed cell lines were digested with EcoRI and fractionated through agarose. After Southern blotting, they were hybridized by the ssRNA probe transcribed from the EcoRI-HindIII 7.6 kb insert of pHzE-M (see FIG. 5A). pPAG-N was digested with EcoRI and resulted in the formation of a 7.3 kb and a 5.4 kb fragment. Due to the probe used, the 7.3 kb band was the major band hybridized in the EcoRI digested plasmid pPAG-N and all the transformed cell lines. The 5.4 kb fragment from pPAG-N was weakly hybridized, since the ssRNA probe recognized only 0.3 kb EcoRI-HindIII region of this fragment. The size of this 5.4 kb fragment varies in the transformed cells depending on the sites that ClaI linearized pPAG-N was inserted. FIG. 8C Northern hybridization using the total RNAs extracted from the individual cell lines showed that PAT1 was expressed in all the hem1 transformed cell lines. Persistently infected TNPC1 was a positive control and parental TN368 cell was a negative control. The probe used was the same as in FIG. 8B;

FIG. 9A $TCID_{50}$ assays were performed in the 96 well culture plates to analyze the anti-Hz-1 baculovirus activities of the hem1 transformed cell lines. A starting titer of $10^8$ was used for all the tested viruses. CPEs induced by the viral infection were recorded every 24 h. FIG. 9B β-galactosidase enzyme assay was employed to analyze the anti-AcAK2 virus activities of the hem1 transformed cell lines. 24 well culture plates were used. An m.o.i. of 0.1 was applied to infect individual cell lines. 24 h after viral infection, cells were harvested and a β-galactosidase enzyme assay was performed;

FIG. 10A Southern hybridization showed that the plasmid pPAG-N was inserted in the host genomes. Purified pPAG-N DNA and genomic DNAs from all four transformed cell lines were digested with EcoRI and fractionated through agarose. After Southern blotting, they were hybridized by the ssRNA probe transcribed from the EcoRi-HindIII 7.6 kb insert of pHzE-M. FIG. 10B Northern hybridization experiment revealed that PAT1 is a very abundant RNA species. Persistently infected SFP1 and SFP2 were positive controls and neomycin resistant gene transfected SFPKN and parental SF9 cells were negative controls;

FIG. 14A Clones containing nest deleted promoters which drive an intact LacZ protein encoding sequence. Bold bars represent the hem1 promoter and the 5' end of PAT1 up to +29 site. CAAT and TATA boxes and GATA (TTATC) motif are shown. FIG. 14B Transient expression of different hem1 promoter deleted constructs determined by LacZ activity.

DETAILED DESCRIPTION OF THE INVENTION

Figure 1A:
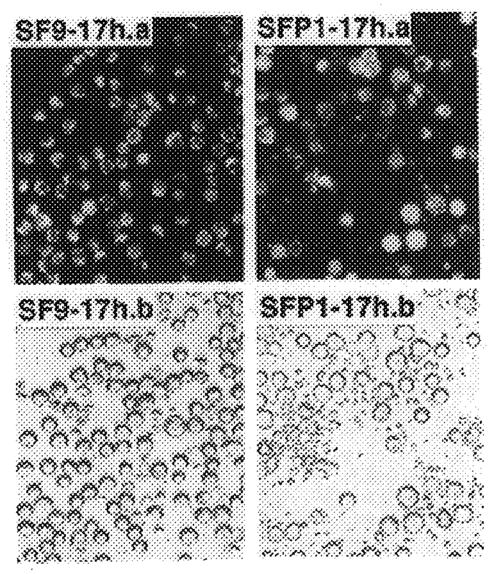
FIGS. 1A and 1B. Appearance of cell cultures at various times after infection with the Hz-1 baculovirus. Parental SF9 cells and persistently infected SFP1 and SFP2 cells were inoculated with an m.o.i. of 5 of the Hz-1 baculovirus, and then either subjected to rhodamine 123 staining, as described in the section of Materials and Methods of the following Example I, or left unstained.

Apoptosis is a distinct type of cell death that differs fundamentally from degenerative death or necrosis in its nature and biological significance. The earliest definitive changes in apoptosis that have been detected with the electron microscope are the compaction of the nuclear chromatin into sharply circumscribed, uniformly dense masses that abut on the nuclear envelope and the condensation of the cytoplasm, subsequently leading to the formation of membrane-bound apoptotic bodies. There is evidence that apoptosis is an active process of gene-directed cellular self-destruction and that in most of the circumstances in which it occurs, it serves a biologically meaningful, hemostatic function. Support for the apoptosis concept is provided by studies of the ultrastructure, biochemistry and incidence of cell death.

A major function of the cellular immune system is the combating of viral infections. It is attractive to speculate that this system made opportunistic use during evolution of a preexisting cell-deletion mechanism that enabled it to eliminate virus-infected cells with minimal tissue disruption. The early fragmentation of DNA in apoptosis may be particularly important in viral containment, since it could halt viral replication and possibly also inactivate an already assembled DNA virus within minutes of contact between a cytotoxic lymphocyte and an infected cell. The general biological function of the DNA fragmentation may be the prevention of the transfer of intact genetic material when apoptotic bodies are phagocytosed. It was also reported that apoptosis occurs spontaneously in virtually all malignant tumors, often markedly retarding their growth. Because of the selective regulation of apoptosis, the capacity to control apoptosis in diseased tissue would have major medical consequences (J. F. R. Kerr and B. V. Harmon, "Definition and Incidence of Apoptosis: A Historical Perspective," in *Apoptosis: The Molecular Basis of Cell Death*, L. D. Tomei and D. C. Frederick, Cold Spring Harbor Laboratory Press, 1991).

In addition to organismal and cellular functions, apoptosis also appears to be an important factor in the replication strategies of viruses in a variety of eukaryotic cells. A number of disparate viruses are known to trigger apoptosis during infection, and members of at least three different virus families, Herpesviridae, Adenovirdae and Baculoviridace, possess genes which can prevent apoptotic cell death of their host cells. Inhibition of apoptosis has also been correlated with viral latency and persistence (Rollie J. Clem and Lois K. Miller, *J. Virol.*, July 1993, p. 3730–3738).

The establishment of long-term infections in which the viruses, some of which are highly cytocidal, continue to multiply while the host animal or cells continue to grow or divide are referred to as persistent infections. According to the classification scheme of persistent infection outlined by C. A. Mims ("Role of persisitence in viral pathogenesis," in

*Virus Persistence*, Mahy, B. W. J., Minson, A. C. and Darby, G. K., eds., Cambridge University Press, Cambridge, January, 1982), there are three ways a virus can be persistent in its host cell. First, the virus can persist without the shedding of the infectious virus; second, the infectious virus may be shed only periodically; and third, virus replication and release occur continuously. Only the latter two types of persistence have been documented with baculoviruses. The persistent infection of vertebrate viruses are modulated by many factors. Some of these are host factors such as cellular permissiveness, immune responses including antiviral antibodies, and intracellular antiviral factors such as interferon. Other factors are virus-derived. These include defective interfering particles, viral structural proteins, temperature-sensitive mutants, etc.

One feature of baculoviruses is their apparent ability to persist in an occult state in the (insect) host through many generations. This persistence is evident in the dramatic onset of virus epizootics in nature. It is not yet understood how these viruses persist in insects or what factors control the maintenance of the persistent state and the induction of infectious virus replication. The study of the persistence of these viruses in cell cultures may possibly provide clues to answering questions in these aspects.

There are currently only two systems in which the persistence of baculoviruses in cell cultures have been studied in detail. One system is the persistence of the nuclear polyhedrosis virus (NPV) of *Spodoptera frugiperda* (SfNPV) in its homologous cell line IPLB-SF-21 (SF), and the best mode is the non-occluded virus Hz-1 (Hz-1V).

The Hz-1 virus is a non-occluded baculovirus (subgroup C of Baculoviridae), and was originally isolated from the persistently infected IMC-Hz-1 cell line established from ovarian tissue of Heliothis zea (Granados, R. R., et al., *Intervirology*, 10: 309–317, 1978; Ralston, A. L., et al., *Virology*, 52: 33–44, 1981). The virus is rod shaped and contains a double-stranded, covalently closed, circular DNA genome of 230 kb. The Hz-1 virus can establish persistent and productive infections in different insect species and several lepidopteran cell lines (H. A. Wood & J. P. Burand, "Persistent and Productive infections with the Hz-1 baculovirus," in *Current Topics in Microbiology and Immunology*, vol. 131: 119–134, 1986; Burand, J. P., et al., "Persistent baculovirus infections," p. 159–175, in *The Biology of Baculoviruses*, edited by R. R. Grannados & B. A. Federici, CRC Press, Inc., New York, 1986). Burand et al (*J. General Virol.*, 64:391–398, 1983b) showed that defective virus particles are generated following serial passage in vitro and are required for the establishment of persistent infections. The defective virus particle samples always contained a small amount of the standard virus as a helper virus. The defective virus particles were shown to interfere with infection or replication of the standard particles (J. P. Burand & H. A. Wood, *J. General Virol.*, 67: 167–173, 1986).

The standard Hz-1 virus particles contain a superhelical, circular, double-stranded DNA genome of 228 to 245 kb. Based on restriction enzyme profiles and electron microscopic contour measurements of DNA molecules, the Hz-1 defective interfering (DI) particles were shown to be heterogeneous in size (Y. Huang, et al., *J. Virol.*, 43: 174–181, 1982; Burand et al., 1983b, supra). DI particle DNAs were estimated to have deletions ranging from 92 to 130 kb. Studies of Hz-1 viral DNA replication and virus-induced protein synthesis have been conducted following inoculations with standard and standard plus DI particles (Burand & Wood, 1986, supra; Burand et al. , 1983b, supra; Burard et al., *J. Virol.*, 46: 137–142, 1983a). These studies documented the translational events involved in productive replication and the early events in establishing persistent infections.

Cellular permissiveness for virus multiplication is influenced by a variety of factors, some of which can interfere with virus replication and consequently affect the development and maintenance of persistent infections. In addition to providing evidence for the action of DI, the studies of Ralston et al (*Virology*, 115:33, 1981) also implicated cell type as a factor affecting the establishment and possibly the maintenance of the Hz-1V persistent infection. The obtained results are consistent with the finding that persistent infections of vertebrate viruses are affected by cell type, possibly through the generation and amplification of DI particles.

Interferon or other intracellular antiviral substances such as antiviral antibodies also interfere with virus replication, resulting in abortive infections and DI particles. Experimental biochemical evidence of such a factor has yet to be presented. On the other hand, virus-derived factors other than defective-interfering particles have been shown to interfere with standard vertebrate virus infection in insect cell cultures. For example, a recent study with vesicular stomatitis virus (VSV) in many cell types has suggested a possible mechanism for interference for virus coat protein (Whitaker-Dowling, P., et al., *Virology*, 131: 137, 1983). VSV transmembrane glycoprotein G synthesis results in the development of a superinfection exclusion where the ability of the infected cells to take up the virus is diminished. It was also found that the resistance to superinfections by persistently infected cultures is only to homologous viruses in the case of Hz-1V, indicating that a factor of viral origin, DI particles, functions in modulating infection, while that exhibited by SfNVP is more general in nature, surmising that a more general antibaculoviral factor(s), perhaps of cellular origin, may control the SfNVP persistent infection.

To more completely understand these processes, the present inventor generated a physical map of the Hz-1 genome. Inasmuch as deletions in the genome play a role in the establishment of persistent infections, the inventor also identified the areas of the genome that are deleted in DI particles. The restriction map of the 228 kb genome of the Hz-1 standard baculovirus was constructed for XhoI, HindIII, EcoRI, SstII and SmaI, using cosmid pVK102 and pBluescript vectors. The genome does not contain a NotI restriction site. Three regions of the genome were unclonable and were mapped by isolation of DNA fragments, in vitro labelling and Southern hybridization procedures. Serial passage in tissue culture was used to produced DI particles. The majority of DI particles in five virus isolates contained genomic deletions ranging from 24 to 52 kb in the 22 to 45 map unit region (Yu-Chan Chao et al., *J. General Virol.*, 71: 1265–1270, 1990).

Based on the studies upon the physical map of the viral genome, the inventor then continued to investigate the construction of an Hz-1 transcriptional map during the course of prodcutive infections, in an attempt to locate genes responsible for turning off host protein synthesis and for cell lysis, and to locate regions of the genome involved in the establishment and maintenance of persistent infections.

Hz-1 viral replication in cell cultures has been studied. The infectious extracellular virus was first detected 12 hours postinfection. At this time, virus-infected TN368 cells appeared round and 20 to 30% of the cells were lysed, indicating that the complete replication cycle of the Hz-1 virus matures before 12 hours. Studies of DNA replication and virus-induced protein synthesis have been conducted.

On the basis of the appearance of the viral proteins, the replication cycle of the virus was divided into three stages: early (0 to 4 h.p.i.), intermediate (4 to 8 h.p.i.), and late (8 to 13 h.p.i.). Very little research has been conducted upon the nature of productive and persistent viral infections, in which the persistent viral infection is suspected to be a common phenomenon in insects.

According to the previously constructed physical map with five restriction enzymes, the present inventor further investigated the regulation of HZ-1 RNA transcription during persistent and productive viral infections. It was found that approximately 100 Hz-1 viral transcripts were identified under conditions of productive replication, whereas only a single major viral transcript was detected in persistently infected cells.

This transcript was found to have a constitutively expressed early RNA analog transcribed during productive viral replication. The region of the viral DNA encoding this viral persistency-associated transcript (PAT1) was located in the EcoRI-M fragment (viz. within 21.8–29.7 map units) of the viral genome and this gene (now named as hem1 in accordance with the position thereof in the restriction map of Hz-1 viral genome) was cloned and its transcription initiation and termination sites and detailed nucleotide sequence were investigated to determine the location from where a corresponding mRNA may be transcribed. It was believed that said gene was a key discovery in uncovering the mysterious mechanisms of persistent baculovirus infection (Yu-Chan Chao et al., *J. Virol.*, March 1992, p. 1442–1448).

Inasmuch as persistently infected host cells appear to be resistant to further infection by a broad spectrum of baculoviruses, in order to evidence that hem1 is an antiviral gene, this gene was ligated to a Drosophila heat shock promoter driven neomycin resistant gene and subsequently incorporated into TN368 and SF9 insect cells. It was found that although the cells were not persistently infected, they appeared to be virus-resistant, and such an antiviral effect is attributed to apoptosis. In the case of normal conditions, if a virus contaminates healthy host cells, it would require 13–24 hours to reach maturation and progeny replication; when viral replication is completed, the host cell are lead to bring out necrosis. It was found, however, that when a virus infected host cells containing the hem1 gene, apoptosis of the host cells took place within 6–17 hours, rendering the virus unable to replicate in said host cells at all.

Based on these findings, it is expected that apoptosis may become a useful tool for the treatment of persistent viral infection diseases, which represent to date a serious medical problem but are very difficult to treat. In addition, since hem1 is the only gene which expresses during persistent viral infection, it may be important to the induction of persistent viral infection, and/or maintenance, and/or reactivation, and/or responsible for the superinfection-induced apoptosis and in turn responsible for viral interference.

The possible function of hem1 was further explored and evidences suggest strongly that the RNA product of hem1, persistency-associated transcript (PAT1), does not encode any protein. These results suggest that PAT1 viral resistance on the host cells functions at the RNA level. It was further found that striking similarities exist between PAT1 and two mammalian transcripts Xist and XIST, which have been implicated in the inactivation of the X chromosome in females (Oldstone, M., *Cell* 56:517–520, 1989; J. G. Spivack and N. W. Fraser, *J. Virol.*, 62:1479–1485, 1988; J. G. Stevens et al., *Science*, 235:1056–1059, 1987; Y. C. Chao et al., *J. Virol.*, 66:1442–1448, 1992).

EXAMPLE I

Superinfection-induced apoptosis and its correlation with the reduction of viral progeny in cells persistently infected with Hz-1 baculovirus I. Materials and Methods:

Cells and viruses: SF9 and SF21AE (Vaughn et al., In vitro, 13:213–217, 1977) insect cells were grown in modified TNM-FH medium at 26° C. (Burand et al (1983), supra). Cells were maintained as monolayer or suspension cultures. Cloned persistently infected SFP1 and SFP2 cells were established from SF9 and SF21AE cells, respectively, by the procedure described by Burand and Wood (*J. Gen. Virol.*, 67:167–173, 1986). Standard Hz-1 baculovirus was plaque purified from an Hz-1 B1 viral isolate (Chao et al., *J. Virol.*, 66:1442–1448, 1992). The plaque purified 1A clone of AcMNPV was used in this experiment (H. A. Wood, *Virology*, 103:392–399, 1980). AcMNPV mutated at the p35 gene (vAcAnh), which was reported to induce apoptosis (Clem et al., *Science*, 254:1388–1390, 1991), was also used to test whether or not apoptosis is responsible for the viral interfernce (resistance) that resulted in the cells being persistently infected with the virus. Viral infection was performed as described previously (Chao et al (1992), supra).

Identification of necrotic and apoptotic cells: The identification of necrotic and apoptotic cells was based on the morphological changes described and illustrated by Kerr and Harmon (Kerr & Harmon (1991), "Definition and incidence of apoptosis: an historical perspective," p. 5–30, In L. D. Tomei and F. O. Cope (ed.), *Apoptosis: the molecular basis of cell death*, Cold Spring Harbor Laboratory Press, Cold Spring Harbor, N.Y.). Further characterizations of apoptotic cells were assisted by rhodamine 123 (L. B. Chen, *Methods Cell Biol.*, 29:103–123, 1989; R. J. Clem et al., *Science*, 254:1388–1390, 1991) and acridine orange staining (D. G. Christopher et al., *Nature*, 349:612–614, 1991). Staining by rhodamine 123 was performed as follows: Cells were stained with 10 $\mu$g of rhodamine 123 per ml at various times postinfection and incubated at room temperature for 30 min. Afer staining, the cells were washed with phosphate-buffered saline (PBS) three times and examined under a fluorescence microscope. For acridine orange staining, the cells at various times postinfection were fixed with glacial acetic acid-anhydrous methanol (1:3) at room temperature for 5 min. After fixing, the cells were washed twice with PBS containing 0.1% Triton X-100. The cells were then stained with 10 $\mu$g of acridine orange per ml in working solution (10 ml of 0.01M EDTA, 15.5 ml of 1M NaCl, 31.5 ml of 0.4M $Na_2HPO_4$, 18.5 ml of 0.2M citric acid, 24 ml of distilled $H_2O$, final pH 6.0) for 30 min. at room temperature in darkness. After staining, the cells were washed with PBS three times, for 10 min. each time, and examined under a fluorescence microscope.

Immunofluorescent staining of virus-infected cells: Cells in a 24-well plate were infected with the Hz-1 baculovirus at a multiplicity of infection (m.o.i.) of 5. At 17 h.p.i., the cells were fixed by incubation in glacial acetic acid-anhydrous methanol (1:3) solution for 5 min. at room temperature, washed three times with PBS-0.1% bovine serum albumin-0.1% Tritin X-100, and incubated for 1 h at room temperature with rabbit polyclonal anti-Hz-1 baculovirus antibody diluted 1:1,000 in PBS containing 3% bovine serum albumin. After three washes with PBS-0.1% bovine serum albumin-0.1% Triton X-100, a fluorescein isothiocyanate-conjugated goat anti-rabbit immunoglobulin G (heavy and light chains, Zymed Laboratories, South San Francisco, Calif.) was added at a dilution of 1:100 in PBS containing 10% normal goat serum and incubated for 1 h.

Each well was then washed three times with PBS-0.1% bovine serum albumin-0.1 Tritin X-100 and visualized with a fluorescence microscope. Photographs were taken with the same exposure time by using Polaroid 667 ASA 3200 film.

II. Results:

A. Differential host responses upon viral challenge:

Two persistently infected cell lines, SFP1 and SFP2, were established by Hz-1 baculovirus infection of parental SF9 and SF21AE insect cells, respectively. The two persistently infected cell lines together with parental SF9 cells were challenged with an Hz-1 baculovirus inoculum and the infected cells were examined with rhodamine 123, a dye which fluoresces in intact energized mitochondria. During the course of apoptosis, intact energized mitochondria have been reported to be found in apoptotic cells and bodies but not in necrotic cells (L. B. Chen (1989), supra; R. J. Clem et al (1991), supra). It was found that the typical response of parental SF9 cells was necrosis, whereas that of SFP1 and SFP2 cells to Hz-1 baculovirus was apoptosis (FIG. 1).

Figure 1B:
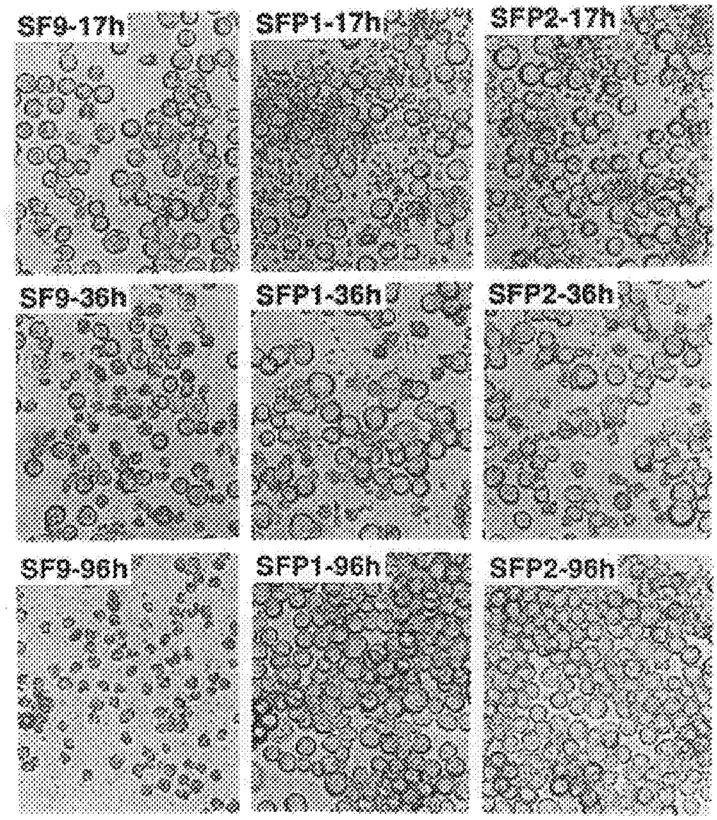

More specifically, necrotic cells were mainly observed in virus-infected SF9 cells and were not stainable by rhodamine 123 (FIG. 1A, SF9-17h.a and SF9-17h.b; FIG. 1B, SF917h). Soon after the viral challenge (17 h.p.i.), some necrotic cells were readily observed in parental SF9 cells and very few apoptotic cells were found in virus-infected parental SF9 cells (FIG. 1A, SF9-17h.a and SF9-17h.b). Within the same time frame, however, much more extensive mortality due to apoptosis was observed in persistently infected cells after virus challenge and many apoptotic bodies were observed in superinfected SFP1 cells (FIG. 1A, SFP1-17h.a and SFP1-17h.b; FIG. 1B, SFP1-17h and SFP1-17h).

Similar significant levels of virus-induced mortality were observed in both parental (FIG. 1B, SF9-36h) and persistently infected cells at 36 h.p.i. (FIG. 1B, SFP1-36h and SFP2-36h). Interestingly, by 96 h.p.i., most of the SF9 cells had died from necrosis (FIG. 1B SF9-96h), whereas persistently infected cells which survived from the initial virus superinfection continued to propagate (FIG. 1B SFP1-96h and SFP2-96h).

Figure 2A:
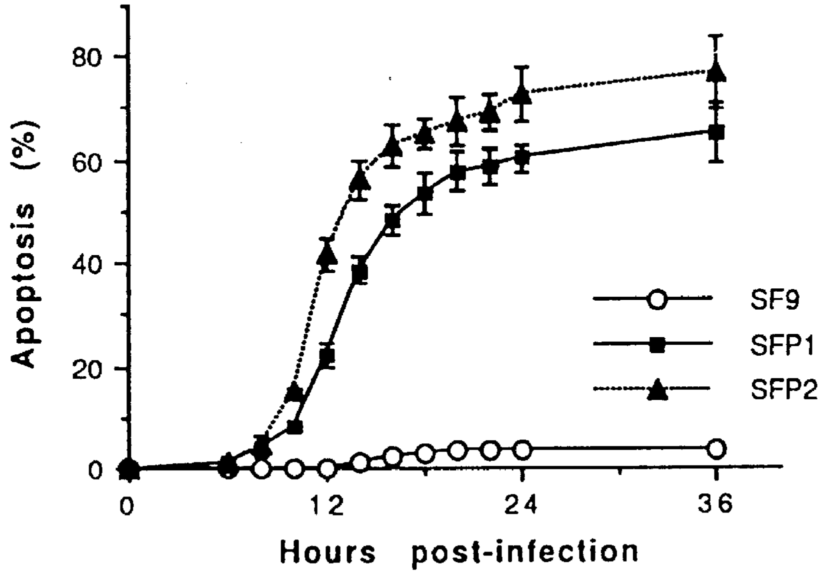
FIGS. 2A–2C. Cell response at various times after the Hz-1 baculovirus infection. Parental and persistently infected cells were challenged with the virus. After viral challenge, the numbers of necrotic FIG. 2A, apoptotic FIG. 2B, and surviving and propagating FIG. 2C cells were calculated as percentages of the cells' numbers before challenge. The Hz-1 baculovirus at an m.o.i. of 5 was used to infect SF9, SFP1 and SFP2 cells. Percentages of necrosis and apoptosis were calculated each time from 200 originally input parental or persistently infected cells. Data (means±standard deviations) were collected from four independent experiments. Symbols: ○, SF9; ■, SFP1; ▲, SFP2.
Figure 2B:
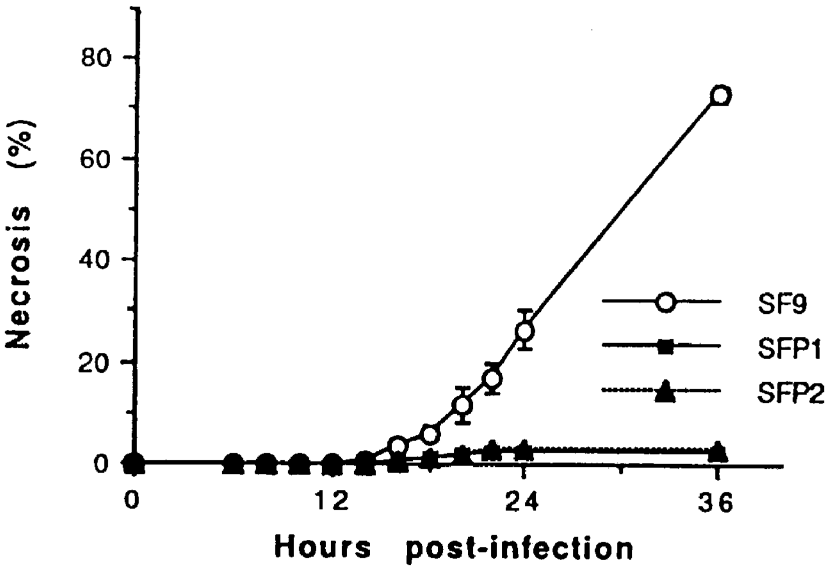

B. Intensive apoptosis upon superinfection of persistently infected cells:

The responses of SF9, SFP1 and SFP2 cells to the virus challenge were traced through time (FIG. 2). Death of the SF9 cells (virus-induced cell lysis) typically began at 13 h.p.i. and increased gradually thereafter. Most of the SF9 cells died from apparent necrosis (FIG. 2A), which is a typical consequence of successful viral infection and replication, as shown previously by transmission electron micrographs of infected cells (Burand et al., "Persistent baculovirus infections," p.159–175, In R. R. Granados and B. A. Federici (ed.), *The Biology of baculovirus*, CRC Press, Inc., Boca Raton, Fla; Ralston et al., *Virology*, 115:33–44, 1981; H. A. Wood and J. P. Burand, "Persistent and productive infection with the Hz-1 baculovirus," *Curr. Top. Microbiol. Immunol.*, 131:119–134, 1986). Less than 4% of these cells died through apoptosis (FIG. 2B).

In contrast, most of the superinfected SFP1 and SFP2 cells died from apoptosis. Apoptosis was first observed at 6 h.p.i., and the percentage of apoptotic cells increased drastically thereafter up to 24 h.p.i. and then leveled off gradually (FIG. 2B).

Figure 2C:
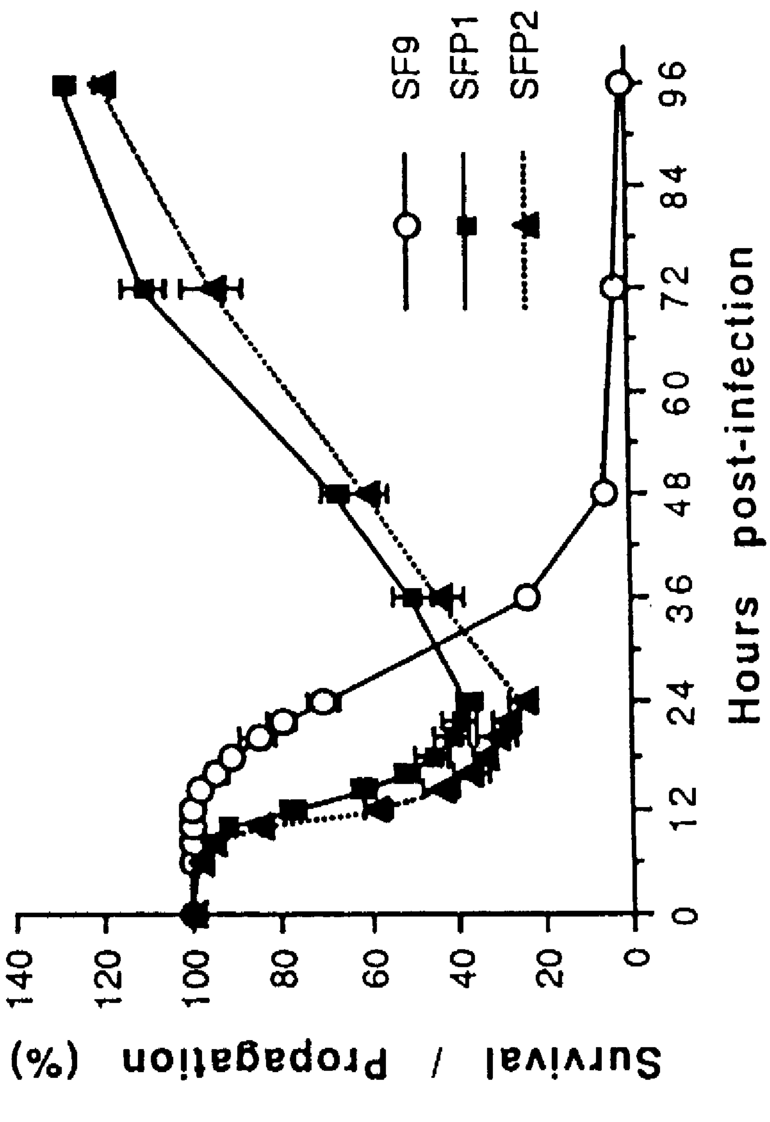

The percentages of the three cell lines that survived and/or propagated after superinfection were also recorded (FIG. 2C). The proportion of surviving cells in all three cell lines decreased rapidly after the viral challenge. Notably, the decrease in the number of surviving cells of the two persistently infected cell lines occurred at a much faster rate than that in the number of surviving parental SF9 cells. The decrease in the number of surviving SF9 cells, although occurring more slowly, proceeded steadily and continuously. At 96 h.p.i., essentially no surviving SF9 cells were observed. For the more rapidly dying SFP1 and SFP2 cells, however, the rate of death was arrested at 24 h.p.i. Thereafter, the cells which survived the initial viral superinfection began to grow (FIG. 2C). Thus, viral homologous interference in persistently infected cells was achieved through a process that combined apoptotic cell death and reestablishment of the host cell population by a subset of surviving cells.

Figure 3A:
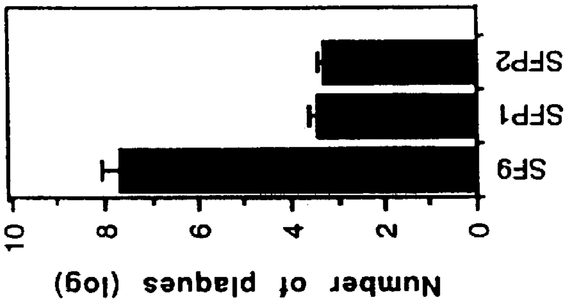
FIGS. 3A–3D. Viral resistance evaluation of different cell lines. The experiments were divided into two parts. In the first part, sensitivity of different cell lines to the direct challenge infection with either Hz-1 baculovirus (A) or AcMNPV (C) was estimated by plaque assay. Hz-1 baculovirus with a titer of $8\times10^7$ PFU/ml (A) and AcMNPV with a titer of $3\times10^8$ PFU/ml (C) were serially diluted 10-fold and then used to infect the SF9, SFP1 and SFP2 cells directly. The plaque formation capabilities of the different cell lines upon virus infection were estimated 5 days postinfection. In the second part, equal numbers ($2\times10^5$) of SF9, SFP1 and SFP2 cells were first infected with either Hz-1 baculovirus (B) or AcMNPV (D) at an m.o.i. of 0.1. Media were harvested daily for 5 days and their virus titers were estimated by plaque assay with SF21AE cells. Data (means±standard deviations) were collected from four independent experiments. Symbols: ○, SF9; ■, SFP1; ▲, SFP2.
Figure 3B:
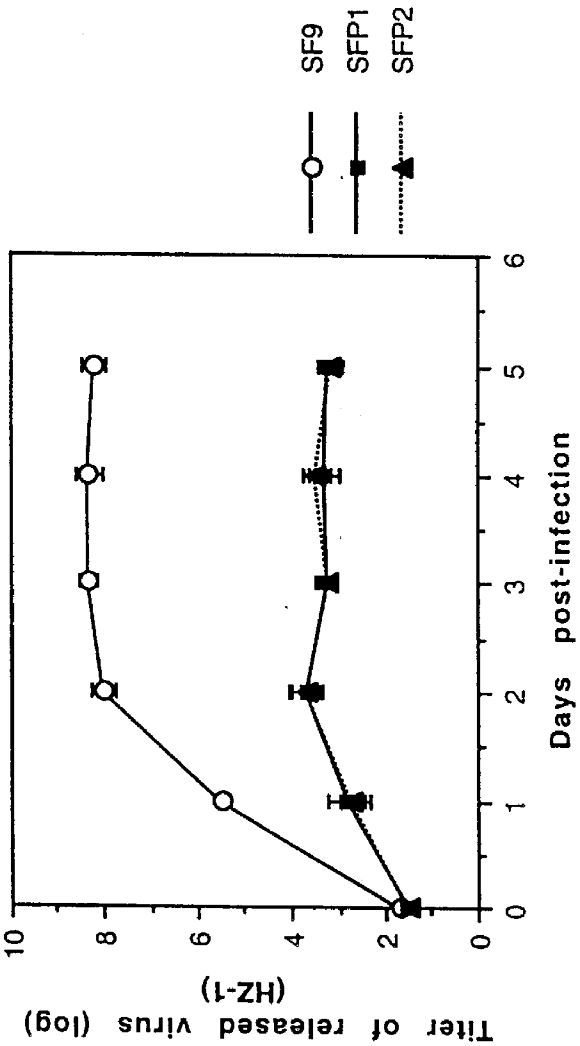

C. Production of viral progeny is greatly reduced in apoptotic cells:

The results of FIGS. 2A–2C collectively suggest that apoptosis occurs so early in persistently infected cells that it may reduce the yield of viral progeny. To test this possibility, both the infectivity and the progeny propagation capability of the Hz-1 baculovirus in parental and persistently infected cells were tested by two different methods. In the first method, the cells were infected directly with the same dosage of the Hz-1 baculovirus and the numbers of plaques formed in these cells were calculated. Numbers of plaques were then plotted as individual bars to represent different cells lines. The results showed that significantly fewer plaques were detected in persistently infected cells than in SF9 cells (FIG. 3A). The second method estimated the yield of viruses produced from different types of cells, giving a titer of released viruses. The numbers of viruses released from superinfected SFP1 and SFP2 cells were decreased $10^4$ to $10^5$-fold compared with those released from parental SF9 cells (FIG. 3B).

Figure 3D:
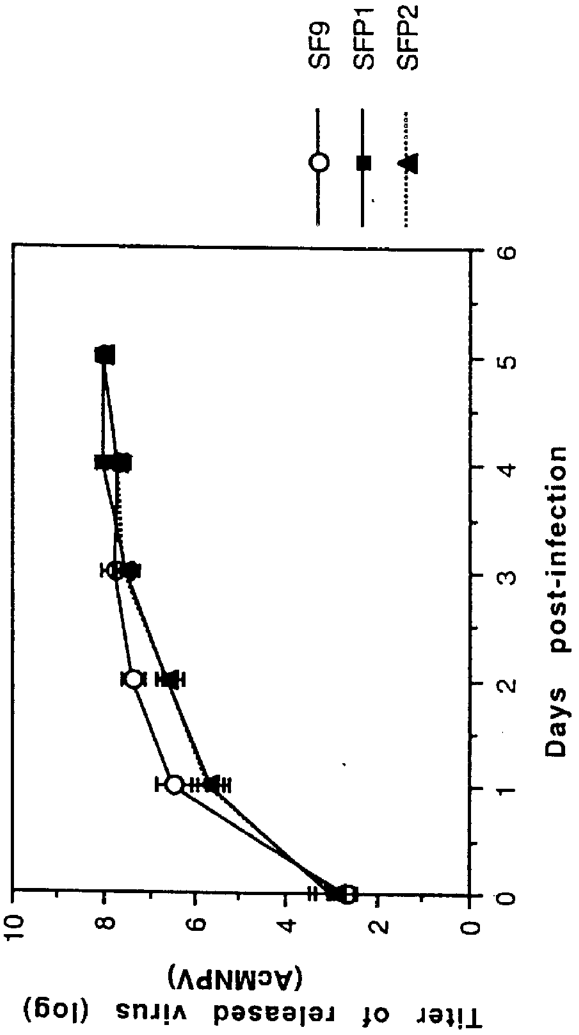
Figure 3C:
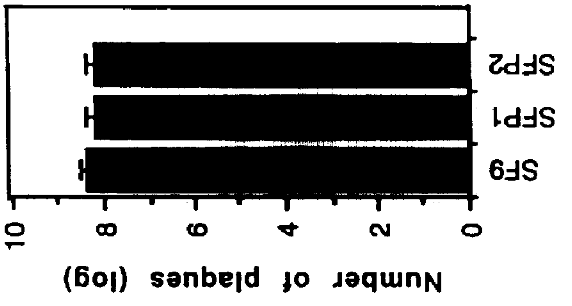

For comparison, a heterologous virus, AcMNPV, belonging to a different subfamily, Eubaculovirinae (M. Wilson, *Arch. Virol. Suppl.*, 2:117–123, 1991), was also used to infect SF9, SFP1, and SFP2 cells. No significant differences were found among the three cell lines either in resistance to AcMNPV infection (FIG. 3C) or in the viruses released from these cells upon viral superinfection (FIG. 3D). These results indicated that the overall production of the Hz-1 baculovirus in persistently infected cells was much less than that in parental cells upon viral challenge.

Figure 4A:
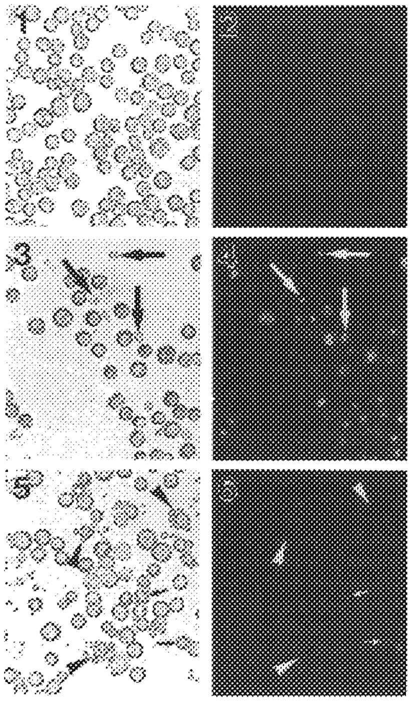
FIGS. 4A and 4B. Immunofluorescence labelling of virus-infected cells. Cells were grown in 24-well plates and infected with Hz-1 baculovirus. At 17 h.p.i., cells were immunofluorescence labelled with an antibody against the Hz-1 baculovirus.

It is interesting and important to know whether the small amounts of viruses detected in superinfected persistently infected cells were generated from apoptotic cells or from necrotic cells which were present in only a small percentage of the superinfected population. To differentiate these two possibilities, fluorescein isothiocyanate-conjugated goat anti-rabbit immunoglobulin G and rabbit polyclonal antibody against the virion of Hz-1 baculovirus were used to label both parental and persistently infected cells at 17 h.p.i. (FIG. 4).

Figure 4B:
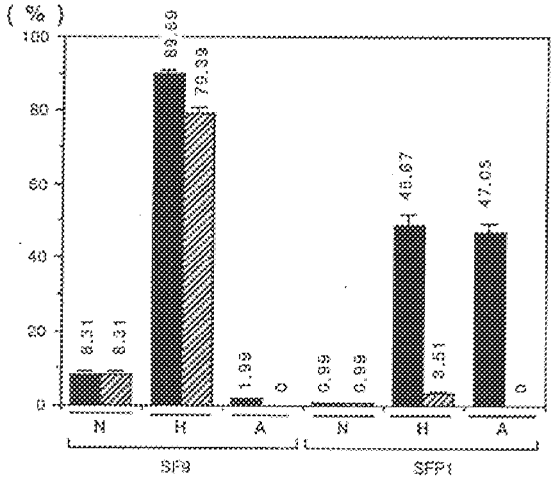

The results showed that the fluorescein isothiocyanate-conjugated antibody did not label mock-infected cells (FIG. 4A, panels 1 and 2), indicating that the antibody did not cross-react with host cells. The fluorescein isothiocyanate-conjugated did strongly label the SF9 cells productively infected with the virus. Essentially all of the necrotic cells were labelled (FIG. 4A, panels 3 and 4, arrows; FIG. 4B column SF9-N). It was also observed that many healthy-looking cells were labelled. Presumably, these were infected cells at stages before cell lysis (FIG. 4A, panels 3 and 4; FIG. 4B, column SF9-H). In contrast, much less intensive antibody labelling was detected in persistently infected cells that were superintected with a virus. Careful examination of the labelled cells revealed that apoptotic bodies were not labelled (FIG. 4A, panels 5 and 6, big arrowheads; FIG. 4B, column SFP1-A). Instead, only necrotic and a few healthy-look-ing cells were labelled (FIG. 4A, panels 5 and 6, small arrows; FIG. 4B, columns SFP1-N and SFP1-H).

As a necessary control, another virus, AcMNPV, was used to challenge SF9, SFP1 and SFP2 cells. AcMNPV has been reported to carry a gene which blocks virus-induced apoptosis in SF-21 cells (E. Martz and D. M. Howell, *Immunol. Today*, 10:79–86, 1989). As predicted, apoptosis was not evident after the AcMNPV infection of cells that were or were not persistently infected with the Hz-1 baculovirus. In addition, the titers of the viruses produced from the parental the cells and cells persistently infected with the Hz-1 baculovirus differed only slightly.

On the other hand, AcMNPV with a mutation in the p35 gene (vAcAnh) has been reported to induce apoptosis in healthy SF21AE cells (Clem et al., (1991), supra). AcMNPV and were thus compared in connection with their effects upon the titer of the released viruses from the infected SF9, SFP1 and SFP2 cells at 48 h post viral infection. The data were displayed in Table 1.

TABLE 1

Titers of the released viruses from the infected cells at 48 h. post infection

| | vAcAnh | AcMNPV |
|---|---|---|
| SF9 | $1.5 \times 10^7$ | $2.5 \times 10^8$ |
| SFP1 | $1.0 \times 10^5$ | $1.5 \times 10^8$ |
| SFP2 | $1.0 \times 10^5$ | $1.0 \times 10^8$ |

With reference to Table 1, vAcAnh induced apoptosis in both SF9 and the persistently infected cells, SFP1 and SFP2. Although once apoptosis was turned on, viral interferences were also observed in the parental cells ($1.0\times10^7$ by vAcAnh vs. $2.5\times10^8$ by AcMNPV), the viral interference was greatly enhanced in cells that were persistently infected with virus (for SFP1, $1.0\times10^5$ by vAcAnh vs. $1.5\times10^8$ by AcMNPV; and for SFP2, $1.0\times10^5$ by vAcAnh vs. $1.0\times10^8$ by AcMNPV).

EXAMPLE II

Hz-1 baculovirus hem1 gene is responsible for the antiviral activity of the persistently infected host insect cells It has long been observed that when an insect host cell is persistently infected by the Hz-1 baculovirus, the host cell becomes resistant to super-infection of a homologous virus, Hz-1 baculovirus, or heterologous viruses, AcMNPV (J. P. Burand et al., Persistent baculovirus infections, p. 159–175, In R. R. Granados and B. A. Federici (ed.), *The Biology of baculovirus*, CRC Press, Inc., Boca Raton, Fla., 1986; A. L. Raltson et al., *Virology*, 115:33–44, 1981; and Wood and Burand, Persistent and productive infections with the Hz-1 baculovirus, *Curr. Top. Microbiol. Innmunol.*, 131:119–134, 1986). Since PAT1 is very abundant and is the only detectable a viral specific RNA species during viral persistent infection, it is reasonable to speculate that viral resistance in the persistently infected cells may be contributed by this unique transcript.

As a consequence, the inventor analysed the nucleotide sequence of the persistency associated gene 1 (pag1, now renamed as hem1 in accordance with the position thereof in the restriction map of Hz-1 viral genome), which is the PAT1 encoding gene, and found that said gene contains no significantly long open reading frame (ORF) . This is an unexpected result. When hem1 was inserted into the genomes of the healthy host cells, originally very susceptible insect host cells became significantly resistant to the infection of the homologous and heterologous baculoviruses. Efforts to identify the protein or peptide translated from PAT1 were failed, also the structure of the PAT1 is very unique, raising the possibility that the host antiviral status contributed by PAT1 may be functional at the RNA level.

Figure 5A:
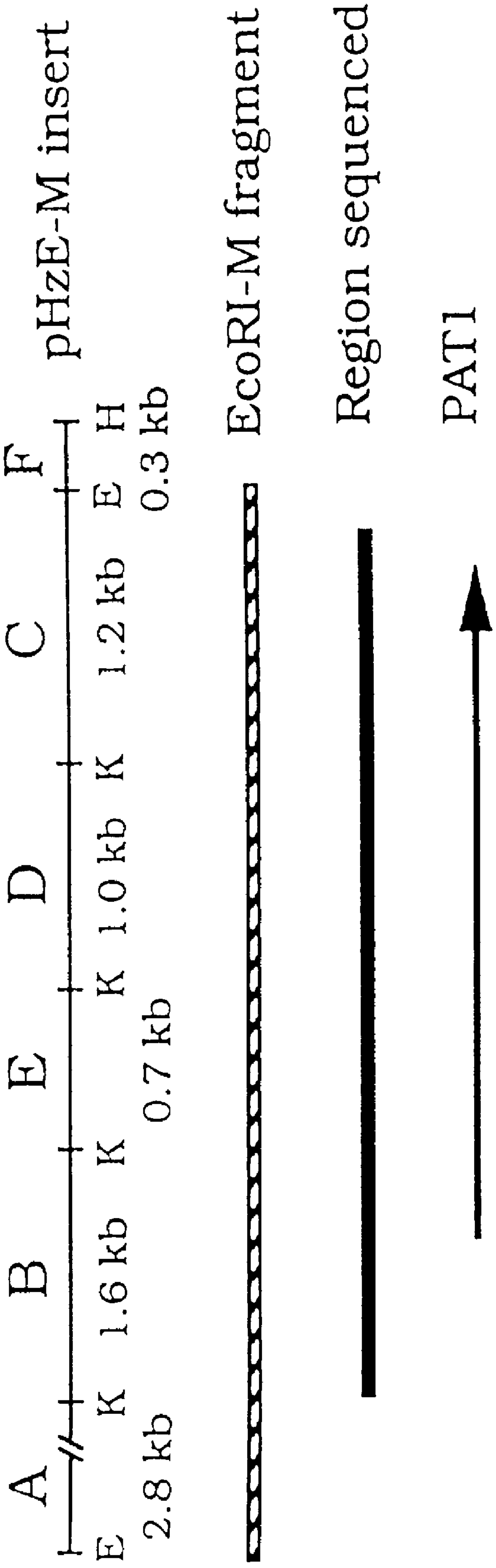

I. Experimental procedures:

A. DNA Sequence determination and analysis:

The entire PAT1 encoding region was found to be contained in the viral EcoRI-M fragment (Chao et al., (1991), supra) . This fragment and an adjacent 0.3 kb EcoRi-HindIII fragment were subcloned together following their viral genomic orientations into a pBluescript vector (Stratagene Co.). The resulting plasmid was named pHzE-M (FIG. 5A). This plasmid was further mapped with KpnI and EcoRI. The digested fragments were assigned as fragments A, B, E, D, C, and F, according to their sizes. Nested sets of deletion clones were constructed from both directions of pHzE-M viral insert using exonuclease III/mung bean nuclease technique (S. Henikoff, *Gene*, 28:351–359, 1984; J. Lawler and R. O. Hynes, *J. Cell. Biol.*, 103:1635–1648, 1986).

The nucleotide sequence was determined using the dideoxynucleotide chain determination method (F. Sanger et al., *Proc. Natl. Acad. Sci. USA*, 75:5463–5467, 1977) directly from double-stranded plasmid DNA. (E. Y. Chen and P. H. Seeburg, *DNA*, 4:165–170, 1985). The modified T7 DNA polymerase (Sequenase™) was used in the sequencing reaction mixture (Tabor and Richardson, *Proc. Natl. Acad. Sci. USA*, 84:4767–4771, 1987). Both strands were sequenced, and each base was sequenced at least two times. DNA sequence analysis was done by using Sequence Analysis Software Package of the Genetics Computer Group (University of Wisconsin, Biotechnology Center). The search for homologies with other nucleotide sequences were accomplished with the “Strings” and “Bestfit” programs; prediction of RNA secondary structure was done using the “Fold” program; prediction of the protein encoding sequence was done using the “Testcode” and “Codon Preference” programs.

B. Cell Cultures and DNA Transformation:

Cultured TN363 or IPLB-SF-21 cells were maintained in TNM-FH medium containing 10% fetal bovine serum (Y. C. Chao et al, Bulletin of the Institute of Zoology, Academic Sinica, Monograph 15:33–47, 1990a) Persistently infected TNPC 1, 2, and 3 cell lines were derived from TN386 cells as described previously (J. P. Burand et al., *J. Gen. Virol.*, 64:391–393, 1983). Plasmid pPAG-N was constructed by inserting a neomycin resistant gene, which is driven by a Drosophila heat shock promoter (H. Steller and V. Pirrota, *EMBO J.*, 4:167–171, 1985), into pHzE-M using the unique HindIII site. Thus the pPAG-N transformed cell was able to express both hem1 and neomycin resistant gene products. The pPAG-N was transformed into TN368 cells using Lipofectin™ according to the instruction manual (Bethesda Research Laboratories). The resulted G418 (400 μg/ml) resistant colonies were isolated and propagated for further assays.

C. RNA Isolation, Probe Hybridization, and Primer Extension Assays:

Total RNAs from cultured cell lines were prepared as described by F. M. Ausubel et al., (*Current Protocols in Molecular Biology*, John Wiley and Sons, Inc., New York, 1989). For the detection of PAT1 expression in the pPAG-N transformed cell lines, total PNAs were glyoxal treated and fractionated by electrophoresis through 1% agarose gel (E. C. Stephenson, Y. C. Chao et al., *Genes Dev*., 2:1655–1665, 1988). Fractionated RNAs were transferred to Gene Screen filters (NEN Research Products) according to the manufacturer's instructions. For the detection of the pPAG-N insertion in the TN368 cell lines, the total cellular DNAs were extracted as described (Ausubel et al., (1989), supra). Purified genomic DNAs were restricted with EcoRI and fractionated on 1% agarose gel. They were Southern transferred onto Gene Screen filters. Both filters were hybridized with a $^{32}$P-labelled ssDNA probe, that was in vitro transcribed from the plasmid pHzE-M using T3 polymerase (D. A. Melton et al., *Nucl. Acid Res*., 12:7035–7056, 1984).

For the determination of 5' end, a 35 base synthetic primer beginning from position 1109(3') to 1143(5'), (1109) 3'-TCGCAGACCATGATCCACTCACCGAGTAAGAATAA-5' (1143) (SEQ ID NO:2), which is antisense to PAT1 was synthesized, and the total RNAs extracted from persistently infected TNP3 and parental TN368 cells were used to perform the primer extension experiment (FIG. 5).

Figure 8A:
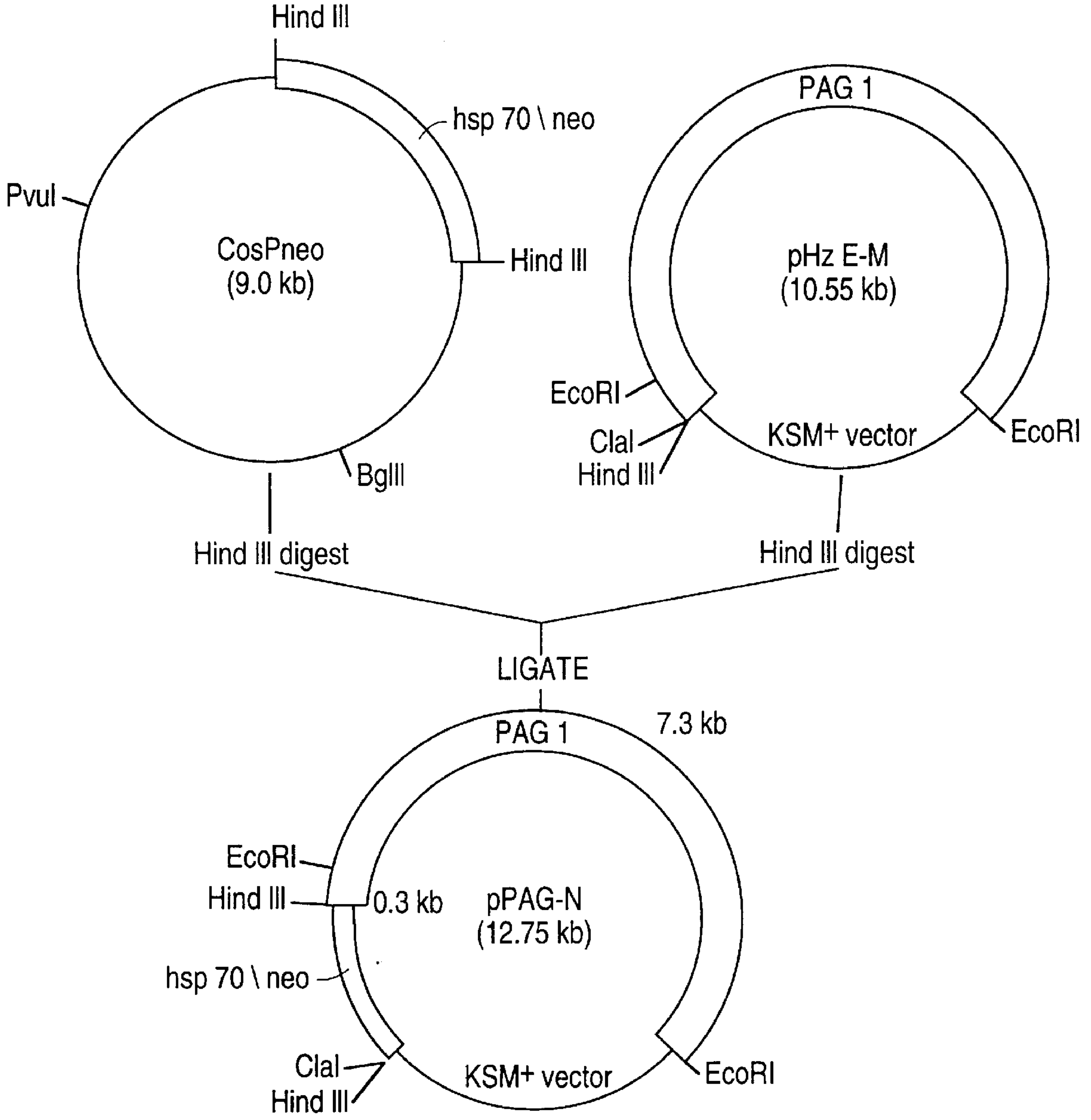
FIGS. 8A–8C.

D. hem1 Transformation:

hem1 gene was ligated with a neomycin resistant gene that is driven by the Drosophila hs70 promoter (Steller and Pirrotta (1985), supra) as shown in FIG. 8A. The resulting plasmid PPAG-N was linearized with the restriction enzyme ClaI and transfected into the healthy TN368 cells using Lipofectin™ (GIBCO BRL Life Technologies Inc.) following manufacturer's instructions E. Virus Stock, Recombinant Virus and Antiviral Assays:

Hz-1 baculovirus was plaque purified standard virus (Chao et al. 1990a, supra). $TCID_{50}$ assays were performed to analyze the antiviral activities of the pag1 transformed cell lines. A starting titer of $10^6$ was used for all the tested viruses. CPEs induced by the viral infection were recorded at 16 h post infection followed by every 24 h. The anti-viral assays were performed five times for the healthy and the hem1 transformed cell lines against Hz-1 baculoviruses.

II. Results:

A. DNA sequencing, primer extension, and RNase protection analyses:

The EcoRI-M fragment and a 3' end adjacent 0.3 kb fragment (referred as F fragment), which ends with a HindIII site, were inserted into the plasmid vector pBluescript to yield pHzE-M (see FIG. 5A). This plasmid was further sub-divided into A, B, C, D, E, and F fragments using restriction enzymes KpnI and EcoRI. These fragments were used to determine the approximate positions of the 5' and 3' ends of PAT1 and it was found that the 5' end is located in fragment B and the 3' end resides in fragment C (Chao et al (1992), supra). Subsequently, it was decided to sequence a region covering fragments B, E, D, and C; nested deleted clones from the viral DNA insert in the plasmid pHzE-M were then made from both directions and sequenced (see FIG. 5).

Figure 5C:
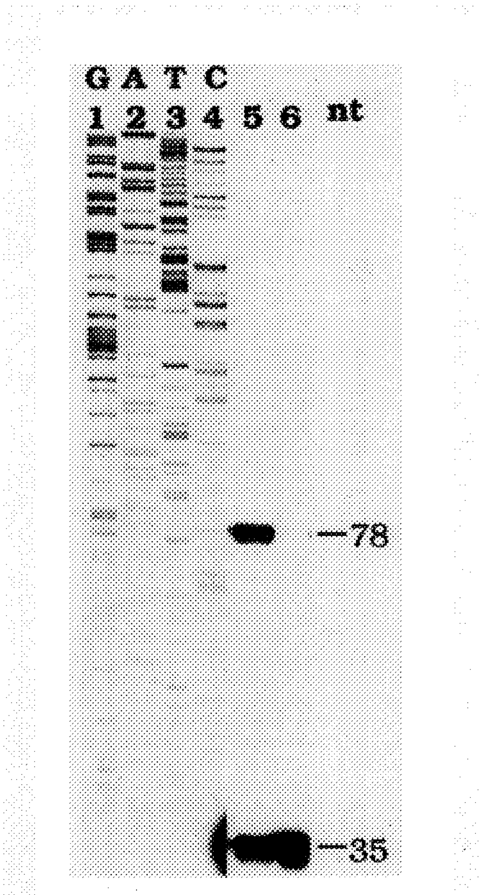

In order to determine the positions of the 5' end, primer extension experiments were performed using a 35 base synthetic primer from 1109(3') to 1143(5') (SEQ ID NO:2). The results as shown in the FIG. 5C indicated that a major 78 base band was extended. This result predicted that the major transcription start site is at position 1066 (FIG. 5, SEQ ID NO:1).

Figure 6A:
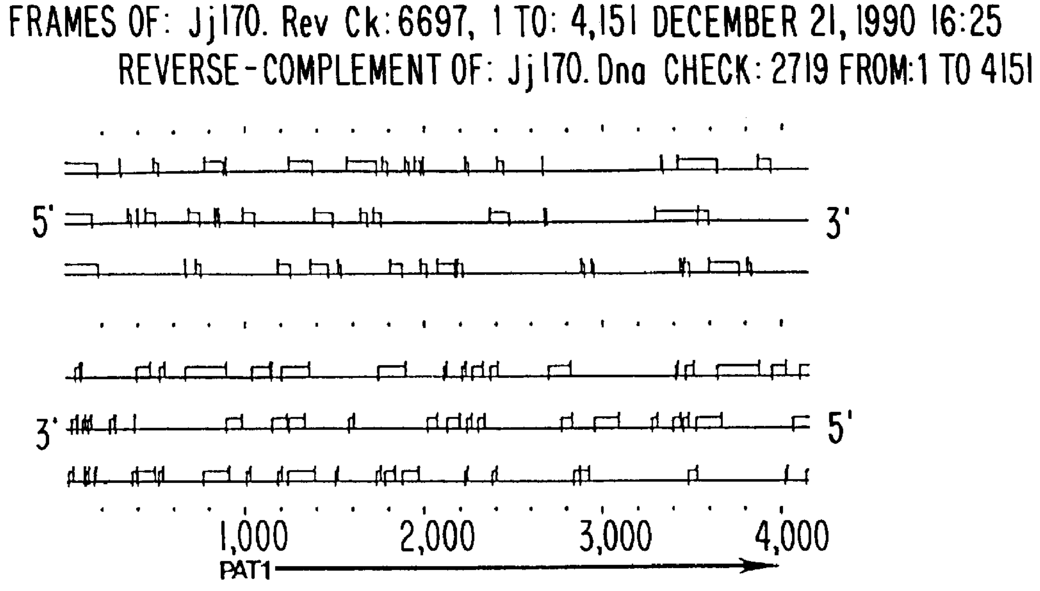
FIGS. 6A and 6B. Computer ORF and testcode analyses of the hem1.

B. Unique gene structure of hem1 (SEQ ID NO:1):

The protein encoding region of hem1 was analyzed by the University of Wisconsin Genetics Computer Group package. The results were unexpected and intriguing. There is no other gene sharing sequence homology with hem1 in the gene bank. In addition, there is no significant long ORF detected in all 6 translation frames. Although the size of the RNA is 2.9 kb, most of the ORFs are smaller than 100 bases (FIG. 6A).

Figure 6B:
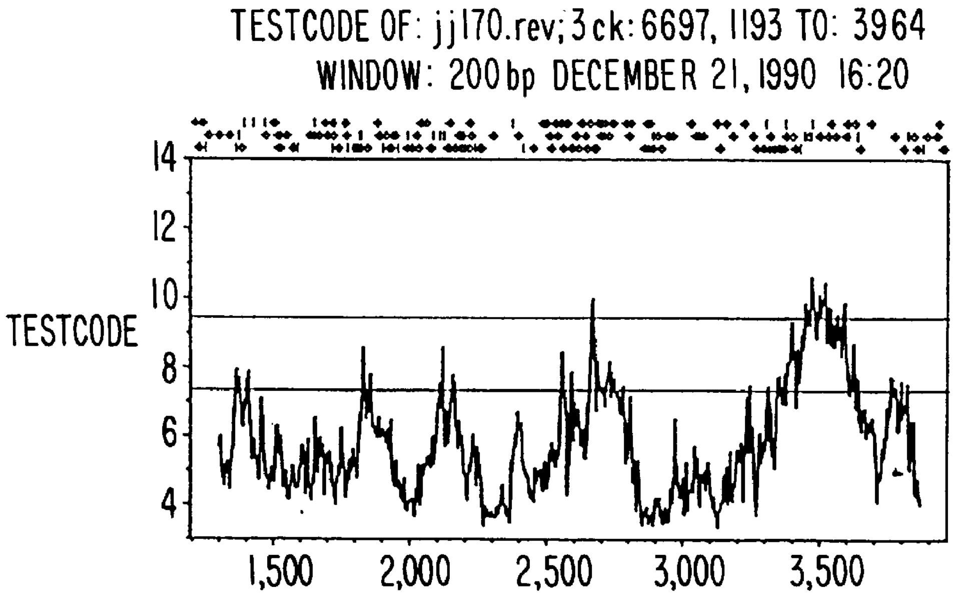

The Testcode program was used to identify possible protein coding sequences by plotting a measure of the non-randomness of the composition at every third base (FIG. 6B). The statistic is independent of the reading frame and is based on measurements of the period three compositional constraints in the entire data base for regions thought to be protein coding and non-coding. The plot is divided into three regions for which the statistic makes a prediction. The top region is supposed to predict coding regions to a 95% level of confidence. The bottom region is supposed to predict non-coding regions to the same contidence level. The middle region is the zone where the statistic can make no significant prediction.

Figure 7A:
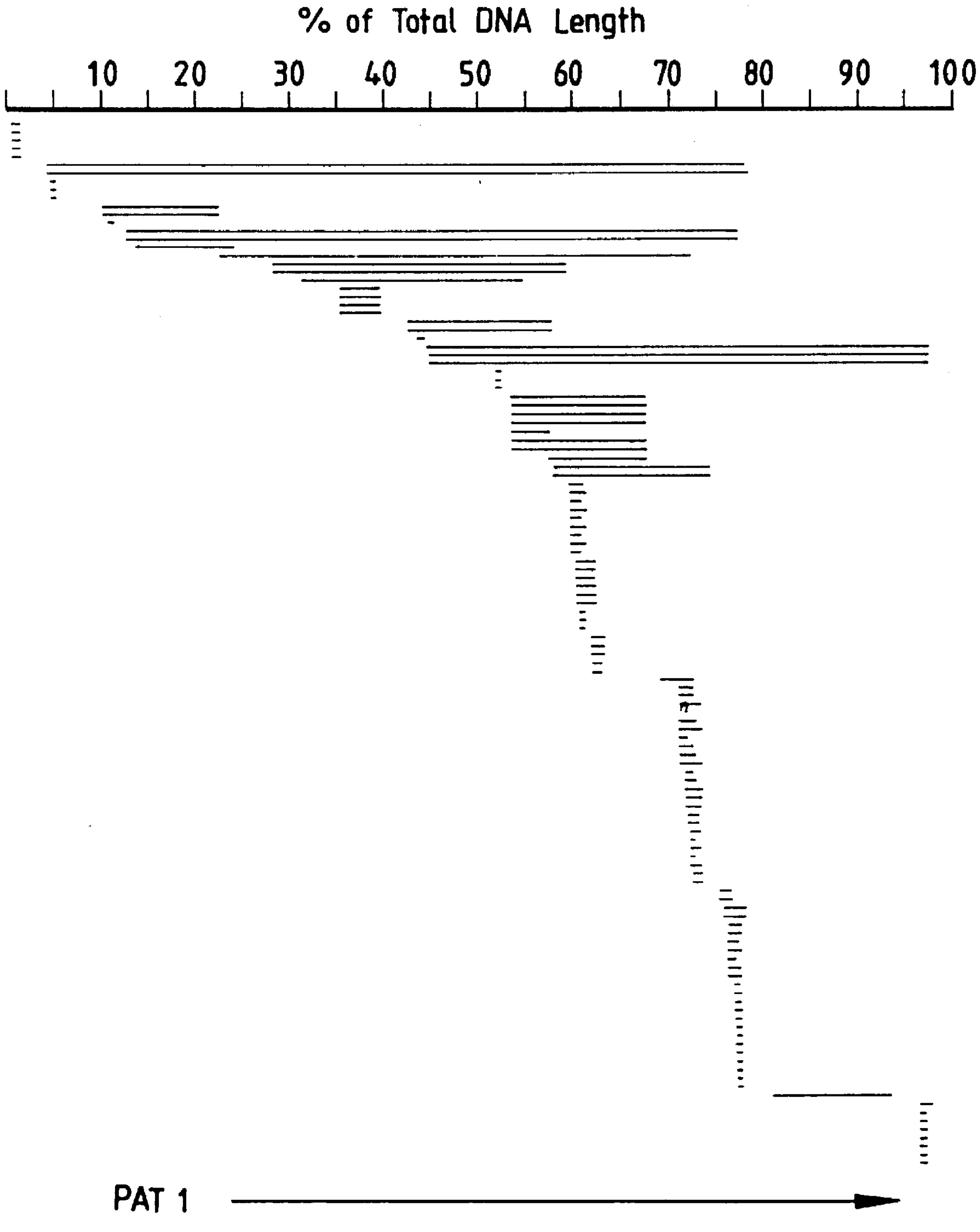
FIGS. 7A and 7B. Analyses of repeat sequences in hem1 and adjacent regions.
Figure 7B:
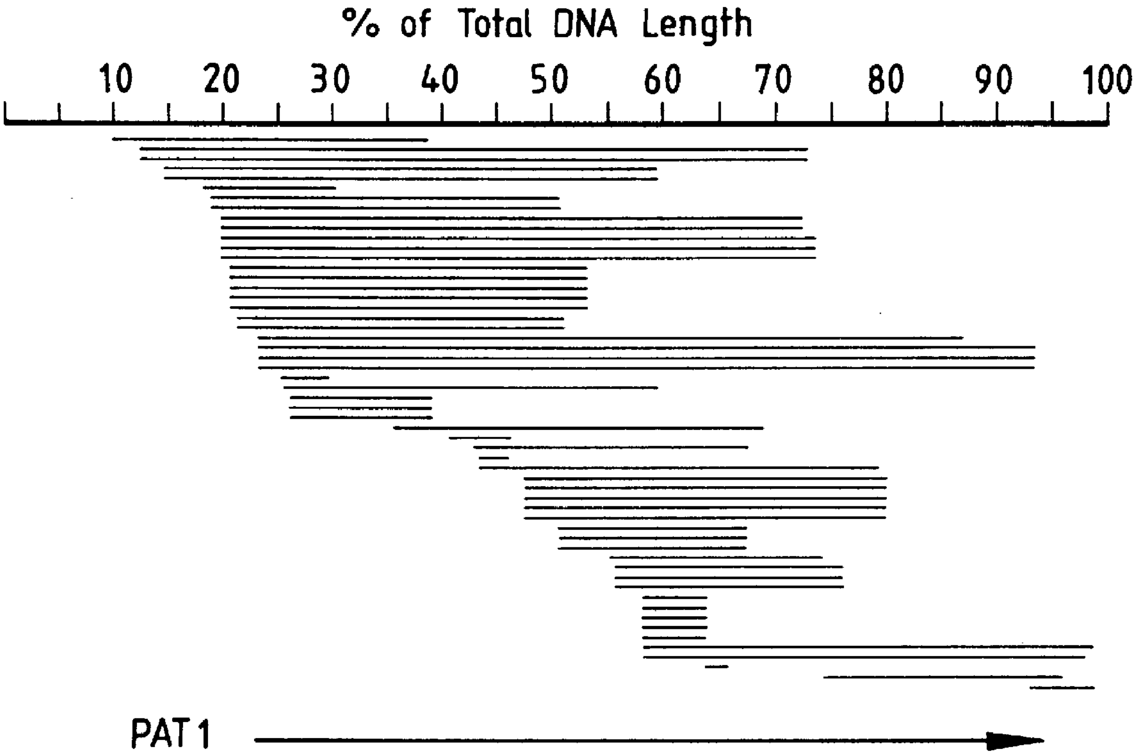

Computer testcode analysis revealed that essentially the entire PAT1 encoding sequence of the hem1 falls into the bottom and to a lesser extent into the middle region. Only a small portion ranging from positions 3400–3600 stretches out slightly into the top region. Such results were a sharp contrast to most of the protein coding genes in which continuous plateaus are usually observed in the top region (J. W. Fickett, *Nucl. Acid Res*., 10:5303–5318, 1982).

hem1 contains large numbers of direct and inverted repeats that are obviously a striking contrast to most other genes (FIG. 7). Computer RNA folding analysis predicted that PAT1 has a very complicated secondary structure. The main axis of the RNA is double stranded with many stems and loops extending out of its main body (data not shown). The computer calculated energy for PAT1 RNA folding using Zuker's program (Zuker and Stiegler, *Nucl. Acid Res*., 9:133–148, 1981) and later defined by Turner (Freier et al., *Proc. Natl. Acad. Sci. USA*, 83:9373–9377, 1986) is very low, −630.1 kcal/mol, indicating the existence of an extensively matched secondary structure.

C. Assay of the function of hem1 product:

Since PAT1 is the only detectable viral specific RNA species during a viral persistent infection, and since its sequence and structure are rather unique, it could be functional at the RNA level. The previous data indicated that during a viral productive infection, three major transcripts, including PAT1, are transcribed through the viral EcoRI-M fragment region. The other two are a 6.6 kb and a >9.4 kb viral specific transcripts. They have different 5' ends, but share similar, if not identical, 3' ends. Northern hybridization analyses revealed the plasmid pHzE-M may contain the promoters for both PAT1 and 6.6 kb RNA only. Due to the unusual length of the >9.4 kb transcript, its promoter certainly exists beyond the viral EcoRI-M fragment and should not be included in the plasmid pHzE-M. The 6.6 kb RNA, however, is expressed 4 h after viral infection. Thus, it is obviously not an immediate early gene product.

Therefore, it was decided to insert the viral DNA contained in the plasmid pHzE-M into the healthy host genome to assay its function in the absence of other viral genome and transcripts. As a first step for introducing this viral DNA into the host cell, a neomycin resistant gene which is driven by a Drosophila heat shock promoter was ligated into pHzE-M and a new plasmid pPAG-N (FIG. 8A) was constructed. Plasmid pPAG-N was then linearized with restriction enzyme ClaI and transfected into healthy TN368 cells. After transfection, over one hundred G418 resistant clones were found. Among these clones, eight of them were further characterized.

The total DNAs were extracted from these pPAG-N permanently transfected lines and also from the untransfected parental TN368 line. These DNAs were subsequently digested with a single restriction enzyme EcoRI and three fragments, a 7.3 kb, a 0.30 kb and a 5.15 kb fragments, resulted from plasmid pPAG-N (FIG. 8A). The first fragment is the viral EcoRI-M fragment, the second fragment is the 0.3 kb EcoRI-HindIII/EcoRI viral fragment and the last fragment is the hsp/neo+vector 5.15 kb fragment. After EcoRI cleavage of the transformed total genomic host DNA, the 7.3 kb EcoRI-M and the 0.3 kb EcoRI-HindIII/EcoRI fragments were generated. However, since the plasmid pPAG-N was linearized from the unique ClaI site before it was inserted into the host genome, the 5.15 kb hsp/neo+ vector fragment was truncated into a 2.25 kb hsp/neo and a 2.9 kb vector fragment. Depending on the position at which the plasmid pPAG-N inserts into the host chromosome, the size of the 2.9 kb vector will vary until the next EcoRI site in the host genome is met.

Figure 8B:
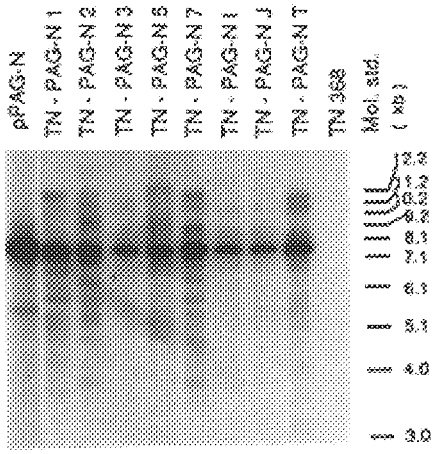

For the Southern detection of the plasmid pPAG-N inserts, a $^{32P}$-labeled antisense ssRNA probe was generated from pHzE-M. This probe contains an entire 7.6 kb inserted viral sequence and a 50 base polylinker sequence of the KSM+ vector (see FIG. 8A). After hybridization, a major 7.3 kb viral EcoRI-M fragment and some minor vector fragments with different sizes were generated. More than one minor bands indicates multiple insertions of the introduced viral gene hem1 (FIG. 8B).

Figure 8C:
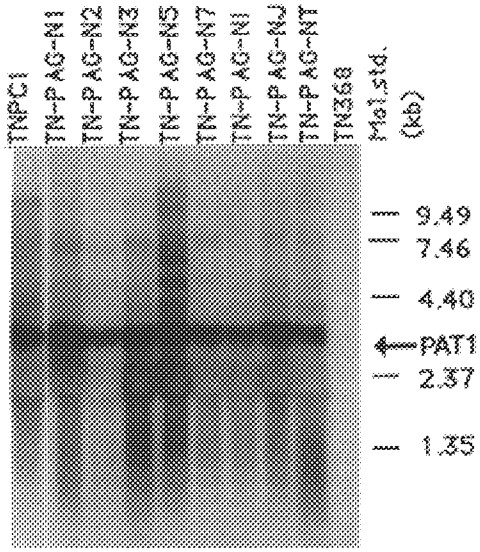
Figure 9A:
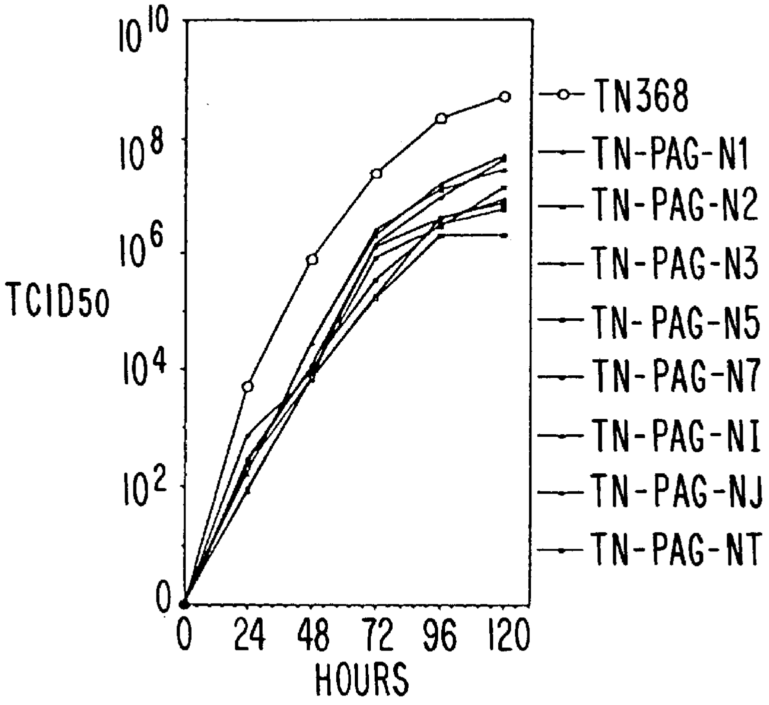
FIGS. 9A and 9B. $TCID_{50}$ and β-galactosidase enzyme assay tests showed that hem1 transformed cell lines are significantly resistant to the haculoviral infections.

The total RNAs were also extracted from all the transformed and control parental cell lines. The same antisense ssRNA probe as described in the above Southern hybridization was used for Northern hybridization. The proper expression of PAT1 was detected in all the transformed cell lines but not the parental cell line (FIG. 8C). These hem1 transformed clones became excellent cell lines for assaying antiviral activity. When challenging these lines with Hz-1 baculoviruses, it was found that all the permanently transfected cell lines were significantly resistant to the homologous Hz-1 baculovirus as compared to the parental TN368 cell line (FIG. 9A).

Figure 9B:
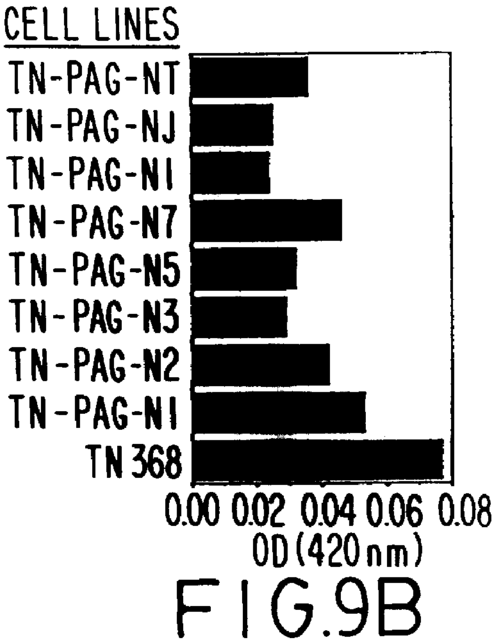

A recombinant AcMNPV which contains a very late promoter (P10 promoter) driving bacteria lacZ gene was also used to assay the antiviral activity of the permanently transfected cell lines to the heterologous baculovirus. The expression of the lacZ gene product was assayed by the β-galactosidase enzyme assay system (Promega Co.). Compared with the TN368 line, the expression of β-galactosidase was significantly decreased in all the permanently transfected cell lines (FIG. 9B). This result indicates that the antiviral activity can extend to heterologous viruses.

III. Discussions:

Based on the analyses upon the PAT1 encoding gene hem1 and its unique and complicated nucleotide sequence, it is exciting to find that the antiviral activity observed from the Hz-1 persistently infected cell line is exerted by the viral gene product PAT1. Furthermore, evidence indicates that PAT1 may be functional at the RNA level.

The observation that hem1 contains no significant long ORF raises the question whether or not any protein or peptide is produced from this gene. It is noted that PAT1 is produced in the persistently infected and permanently transfected (FIG. 8C) cell lines with abundance. However, they are localized in the nucleus and obviously no protein is generated.

The computer testcode analysis did reveal that there is no continuous plateau of codon bias; this is another support for the non-protein encoding nature. The extraordinary numbers of the inverted and direct repeats present in the PAT1 encoding region and the extreme stable and complicated secondary structure predicted by the computer RNA folding analysis suggests that PAT1 is a specially designed molecule which might be functional at the RNA level.

During herpes simplex virus type 1 (HSV-1) latency, three latency-associated transcripts (LATs) were detected within a limited area in the vicinity of the immediate early gene ICPO (Spivack and Fraser, *J. Virol.*, 61:3841–3847, 1987; V. Van Stevens et al., *Nucl. Acid Res.*, 12:7035–7056, 1987). Mutations were later introduced into the viral genomic encoding region of the LATs and it was found simultaneously by different groups that LATs are not responsible for the initiation of latent infection (Steiner et al., *EMBO J.*, 8:505–511, 1989; Ho and Mocarski, *Proc. Natl. Acad. Sci. USA*, 86:7596–7600, 1989), however, some (Dobson et al., *J. Virol.*, 63:3844–3851, 1989; Leib et al., *J. Virol.*, 62:2893–2900, 1989; Steiner et al., (1989), supra) but not all (Block et al., *J. Virol.*, 64:3417–3426, 1990; Ho and Mocarski (1989), supra) LATs mutants suggest that they may be involved in HSV-1 reactivation.

Since the Hz-1 baculovirus is an insect virus, PAT1 may be functional differently from the LAT. Nevertheless, the differential gene expression patterns of Hz-1 baculovirus and HSV showed that there are general similarities in the viral production and persistency switches. Very recently, Zwaagstra et al., (*J. Virol.*, 64:5019–5028, 1990) reported that the LATs may be introns of a larger unstable 8.3 kb RNA. Because the promoter previously predicted for the IRTs is over 660 bases upstream from their transcriptional start site, but only about 28 bases from the newly identified 8.3 kb RNA, raising the doubt that some or all of the LATs are the spliced introns (Zwaagstra et al., 1990, supra). Therefore, they proposed that instead of the small LATs, the 8.3 kb RNA or its spliced transcripts might actually be the functional molecules.

It may currently be ensured that the functional RNA is encoded in the viral insert of the plasmid pHzE-M. Also, hem1 was equipped with a typical polymerase II promoter consensus sequence, which contains a typical TATA box, two CAAT boxes and an AP-1 binding site. The TATA box is 24 bases upstream from the 5' transcription start site of PAT1, which is a sharp contrast to the distance between the LATs and their previously proposed promoter in HSV-1. The possible differential splicing may also explain why the predicted transcription start sites are slightly different between the results of the primer extension and RNase protection experiments.

When pPAG-N plasmid was inserted into the genome of the host cells, PAT1 was expressed in all the examined cell lines. The most interesting finding was that these cell lines were not only resistant significantly to the infection of homologous Hz-1 baculovirus but also to the remotely related subgenus A baculovirus, AcMNPV. All the current evidences indicates that PAT1 is likely to function at the RNA level. It is still very novel today to propose the existence of a functional RNA, especially if this RNA is shown to be a key factor responsible for the viral resistance. Studies on human immunodeficiency virus (HIV) indicated that RNA may be involved in the transcriptional machinery and cumulated evidence showed that TAR (tat-responsive element) may function as nascent RNA form in cis (see Sharp and Marciniak, *Cell*,59:229–230, 1989, for a review). PAT1 instead, is likely to function after it is fully transcribed and acts as an inhibitor for the viral transcription or replication in trans, since the transformed healthy host insect cells which express PAT1 continuously exerted viral resistance to the invading baculoviruses. Also, since the antiviral function of hem1 must be established in nature and tested in nature for an extremely long time, certainly, it should not be a repression mechanism that a baculovirus can overcome easily. It is therefore a unique and very good model for the study of antiviral mechanism.

EXAMPLE III.

Figure 10A:
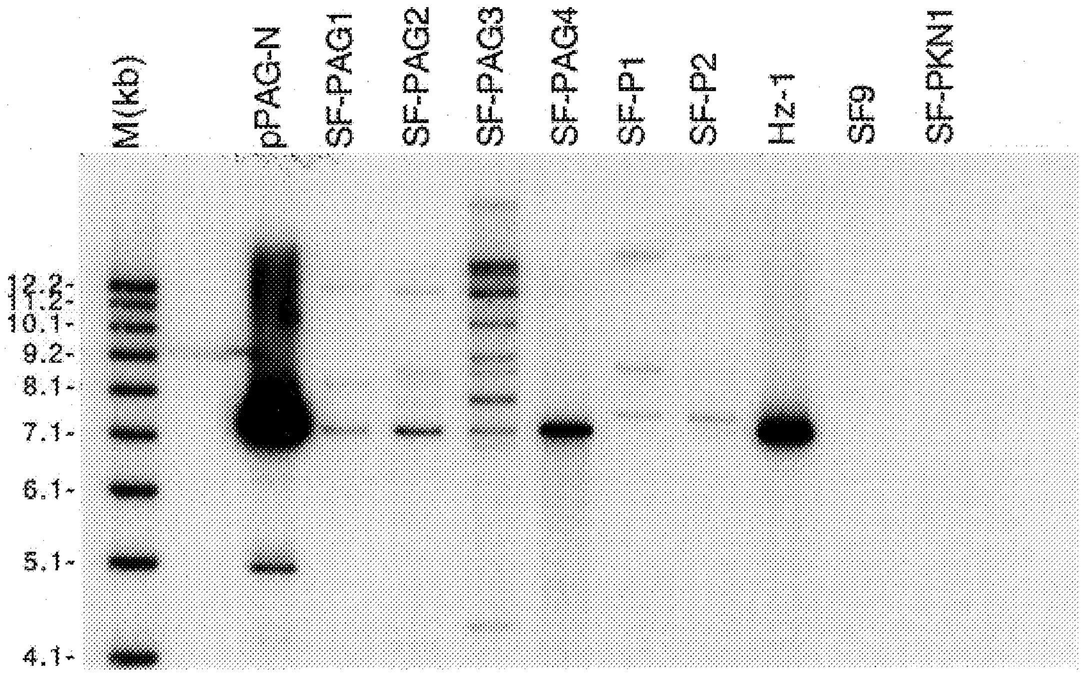
FIGS. 10A and 10B. The successful introduction of hem1 into the insect SF9 cell, which was conducted in subtantially the same manner as that described in FIG. 8.
Figure 10B:
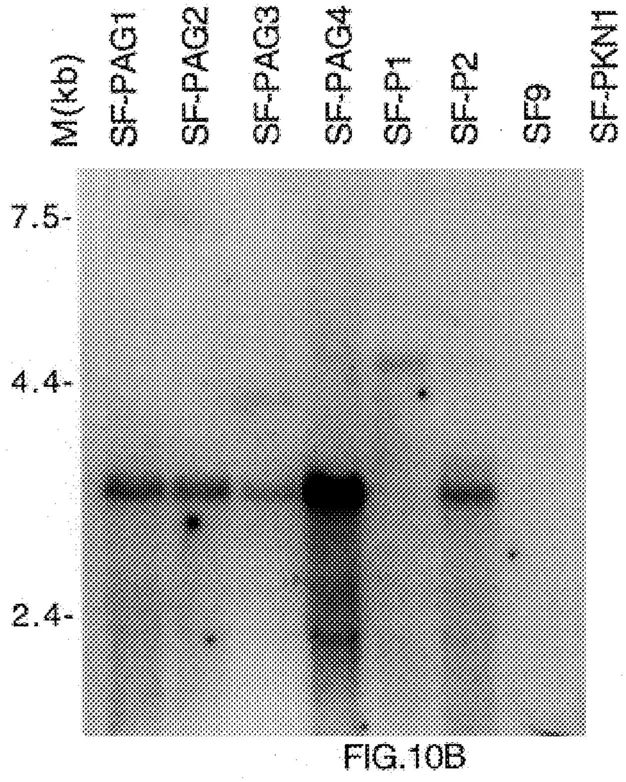
Figure 11:
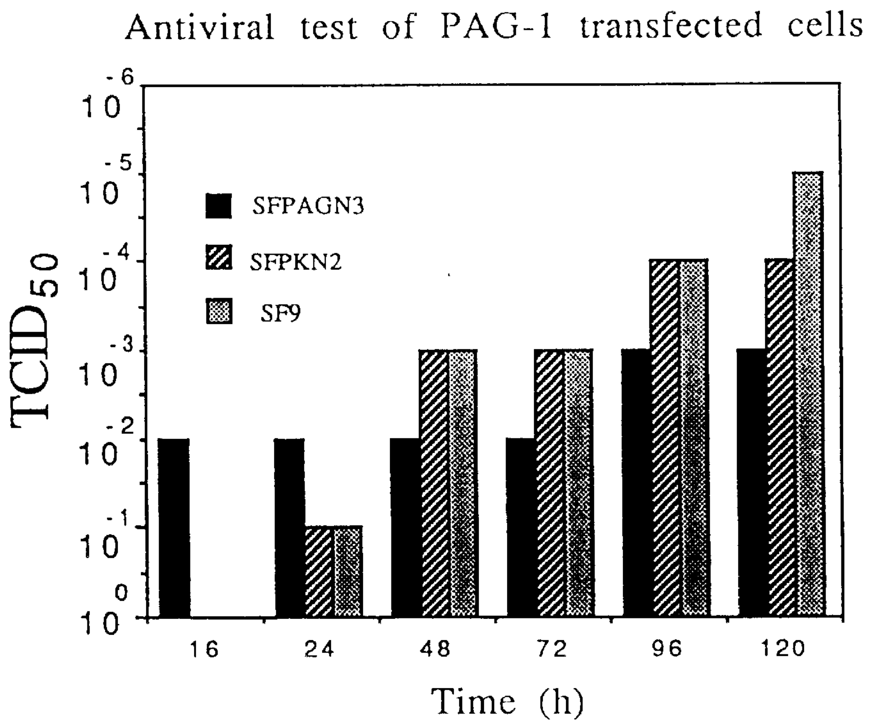
FIG. 11. Viral resistance exerted in the hem1 permanently transfected cell through time. Sensitivity of different cell lines to the direct challenge infection with Hz-1 baculovirus was estimated by plaque assay through time. Hz-1 baculovirus with a titer of $1\times10^5$ PFU/ml was serially diluted 10-fold and used to infect SF9, SFPAG2, and SFPKN2 cells. SF9 is the parental cell; SFPAG2 is hem1 permanently transfected cell; and SFPKN2 is a cell permanently transfected with a neomycin resistant gene.
Figure 12:
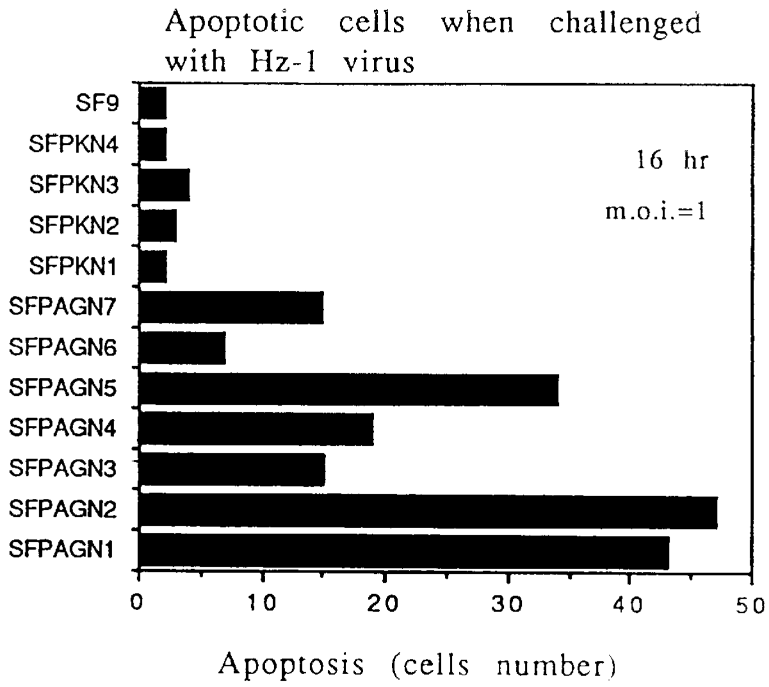
FIG. 12. Response of the different cells upon viral challenge. Parental SF9 cell (SF9), neomycin-transfected cells SF-PKN1,2, and 4, and hem1 permanently transfected cells SF-PAG1,2,3,4,5,6, and 7 were challenged with the Hz-1 baculovirus. The number of apoptic cells were calculated 16 h postinfection from a fraction of 200 original cells.

The effect of hem1 gene in permanently transfected cells established from parental SF9 cells:

The hem1 transformation procedures set forth in the above Example II were repeated except the parental SF9 cells were used. Southern and Northern blotting assays confirmed the successful incorporation of this gene into the SF9 cell genomes (FIGS. 10A and B). It was found that although not persistently infected, these transfected cells also exhibited strong resistance to the superinfection of the virus (FIG. 11). It was further discovered that the antiviral effect is due to the induction of apoptosis in said cells (FIG. 12). Thus, these collected experimental data may promise the use of hem1 as an effective antiviral gene in the prevention of viral infection.

EXAMPLE IV

Hz-1 baculovirus encodes a persistency-accociated RNA analogous to Xist in mammals:

Massive inactivation of large gene regions is an important question in many fields of biology. The mouse Xist (N. Brockdorff et al., *Cell*, 71:515–526, 1992) and human XIST (C. J. Brown et al., *Cell* 71: 527–542, 1992) genes have been implicated in the inactivation of the X chromosome in females. Another phenomenon that involves gene inactivation is latent infection by DNA viruses (Oldstone, M., *Cell* 56:517–520, 1989; J. G. Spivack and N. W. Fraser, *J. Virol*, 62:1479–1485, 1988; J. G. Stevens et al., *Science*, 235:1056–1059, 1987; Y. C. Chao et al., *J. Virol.*, 66:1442–1448, 1992). During persistent infection of insect cells from *Spodoptera frugiperda* (SF21) and *Trichoplusia ni* (TN368) by Hz-1 baculovirus, the expression of viral genes decreases from more than 100 transcripts associated with productive infection to only one transcript.

This expression pattern is very similar to that of other latent viral infection systems. The unique transcript expressed during viral persistency is named persistency-associated transcript 1 (PAT1). It is found here that PAT1, which is expressed upon massive viral gene shut-off in persistent infections, contains no significant open reading frames and is not associated with ribosomes, but accumulates in the nucleus. These results indicate that PAT1 is an entirely new type of viral transcript. In addition, striking similarities between PAT1 and two mammalian transcripts Xist and XIST were found. Whether PAT1 inactivates the expression of its own genome, as do Xist and XIST, or functions by an as yet unknown mechanism becomes an interesting and important issue on persistent viral infection.

Methods and Materials:

A. For polysome fractionation, TN368 cells persistently infected with the Hz-1 baculovirus (TNP3 cells) were used. $1\times10^7$ TNP3 cells were harvested and washed with phosphate-buffered saline (PBS) containing cycloheximide (CHX) and lysed with Triton X-100 plus CHX. Lysates were clarified and then treated either with or without EDTA. The lysates were layered on sucrose gradients (15 to 50% w/v) and sedimented in a Beckman SW41Ti rotor at 32,000 rpm for 130 min. Gradients were fractionated by injecting a 65% sucrose solution and collecting the displaced gradient at the top with an ISCO model 640 gradient fractionator. A UA-5 recorder was used to monitor absorbency at 254 nm during fractionation. Aliquots were cooled, deproteinized, extracted with phenol-chloroform, and then ethanol precipitated. One tenth aliquots of the pellet RNA were assayed by Northern blot.

B. For fractionation of both nuclear and cytoplasmic RNA, $1\times10^7$ persistently infected TNP3 cells were lysed with a lysis buffer containing NP-40, and the nuclei were pelleted by centrifugation at 2000 rpm for 3 min. The supernatant was used for extracting cytoplasmic RNA by phenol extraction and DNase digestion. Nuclear RNA was extracted from the nuclear pellet with guanidine thiocyanate. 5 $\mu$g of the resultant RNAs was serially diluted and slot blotted. Two in vitro transcribed probes containing either the hem1 or the actin sequence were used to hybridize to both Northern blots and slot blots.

C. Nest deletions in the promoter region were generated by polymerase chain reaction (PCP) technology. These synthesized fragments were then ligated to a full-length LacZ encoding sequence in the pUC18 plasmid. All the regions generated by PCR were confirmed by DNA sequencing. $5\times10^5$ SF9 cells were cotransfected with individual LacZ constructs containing nest deleted hem1 promoters (1 $\mu$g) and a construct containing a CAT encoding sequence which is driven by the Drosophila actin promoter (0.25 $\mu$g) as an internal control. At 48 h post-transfection, a fraction equivalent to $2\times10^3$ cells was added to 4-methylumbelliferyl-β-D-galactoside (Sigma Co., USA) and incubated at 37° C. for 30 min. Fluorescence intensity reflected from methylumbelliferone which was derived from the cleavage of 4-methylumbelliferyl-β-D-galactoside by β-galactosidase was measured by TKD-100 fluorometer (Hoefer, Inc., U.S.A.). Experiments were repeated three times for each different promoter construct.

Figure 13A:
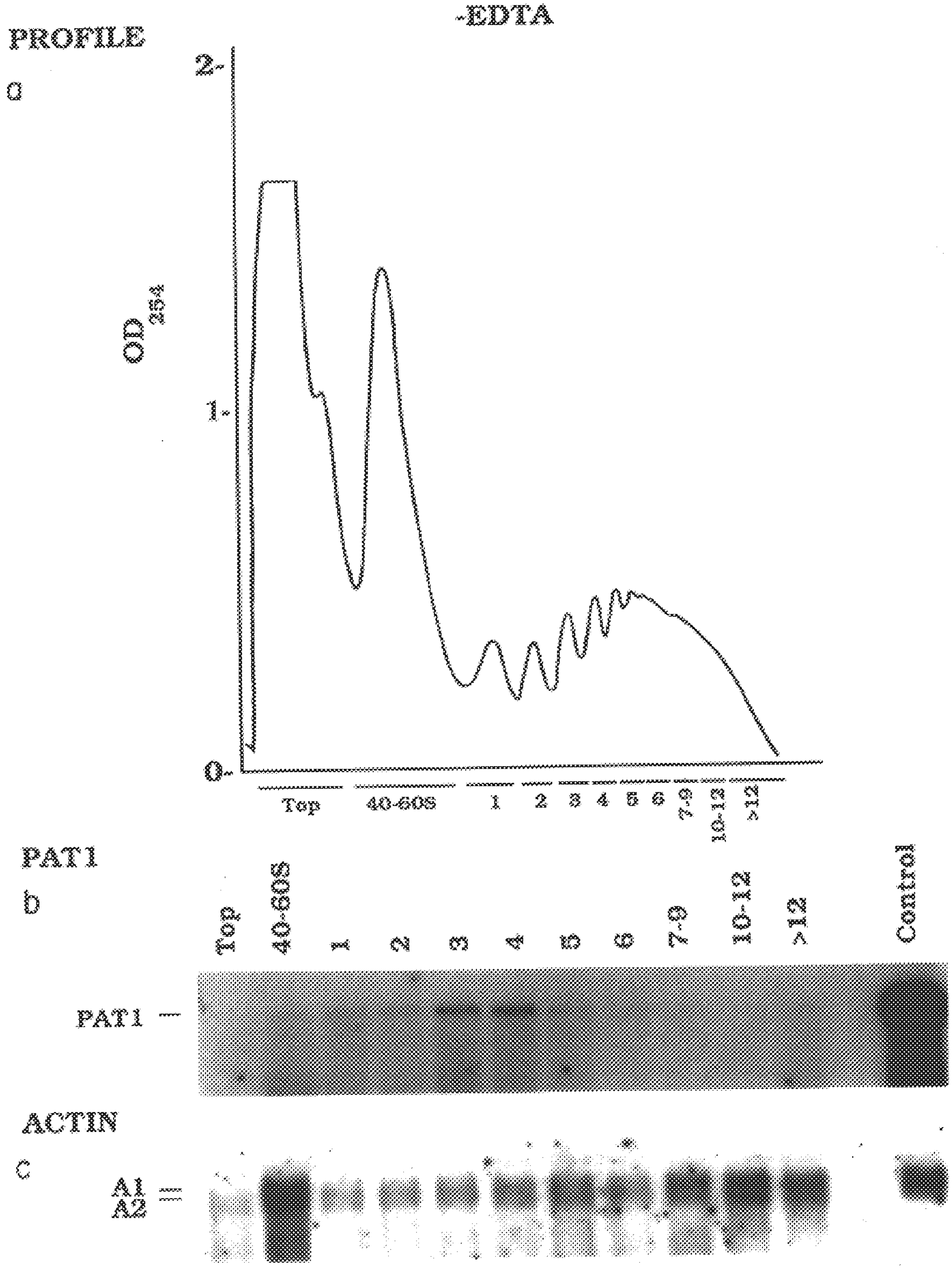
FIGS. 13A–13C. Evidence the non-protein-coding nature of PAT1. Polysomal fractionation of postmitochondrial lysates collected from persistently infected cells without (A) or with (B) addition of EDTA. In both panels (A) and (B), profile of $OD_{254}$ absorbency (a); Northern blotting analysis of polysomal fractions were hybridized with either hem1 (b) or actin (c) probes. Prior to sucrose fractionation, one twelfth of the total RNA which was later loaded onto sucrose gradient, was collected and loaded into the control lanes for RNA titration. (C) Slot blots showing that PAT1 is primarily localized in the nucleus.
Figure 13B:
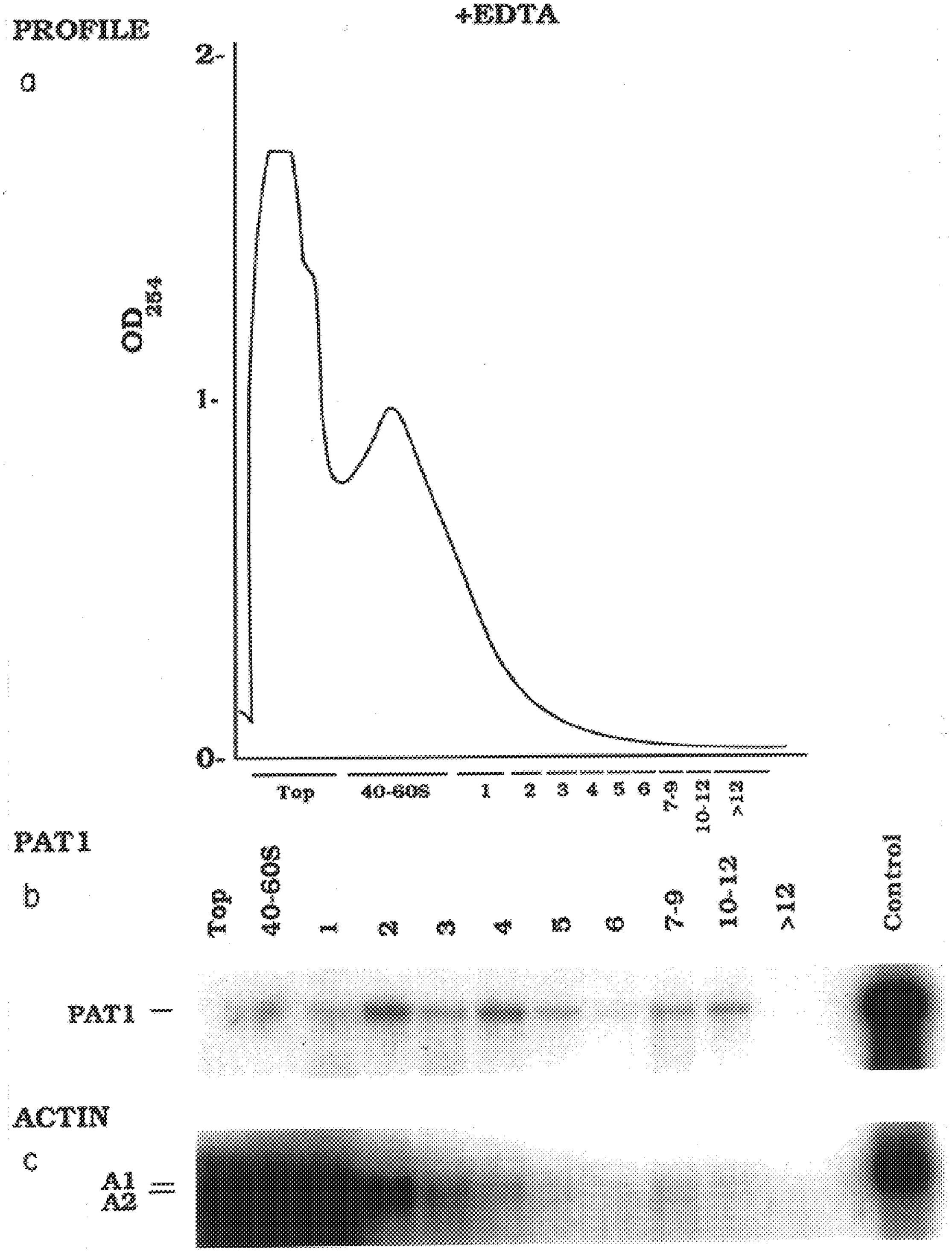

Results:

To further determine whether PAT1 encodes any peptides, the possible association between PAT1 and the cellular protein synthesis machinery was studied. For this purpose, postmitochondrial fractions were obtained from Triton X-100 treated persistently infected cultured cells, derived from TN368 cells. Polysome profiles were subsequently generated by measuring absorbency at 254 nm of fractions collected by sucrose density gradient fractionation. As a control, polysomes were dissociated from mRNA by adding EDTA (S. E. Lee and G. Brawerman, *Biochemistry*, 10:510–516, 1971). Fractions were harvested and analyzed by Northern blotting. A low level of PAT1 was detected throughout the sucrose gradient fractions with or without EDTA treatment (FIG. 13A and B). In contrast, actin mRNA, as a control for translatable mRNA, clearly localized in the heavy polysome binding regions when EDTA was omitted (FIG. 13A). However, in the presence of EDTA, the majority of the actin signals shifted drastically from the heavy polysome fractions to the free ribosomal fractions (FIG. 13B).

Compared to the control lanes of PAT1 and actin, the signal intensity of PAT1 in the postmitochondrial fractions was reduced significantly (panels b and c of FIGS. 13A and B). The low abundance of PAT1 in these fractions suggests that the majority of PAT1 is probably localized in the nucleus.

Figure 13C:
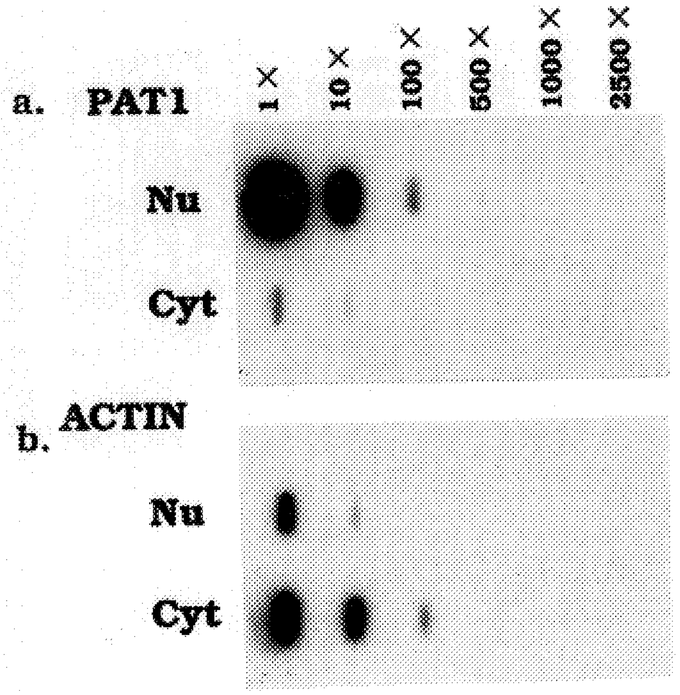

To test whether PAT1 does exhibit nuclear localization, RNAs from both isolated nuclei and pooled cytoplasmic fractions were analyzed. PAT1 was present almost exclusively in the nucleus, with less than 1% of the PAT1 signal occurring in the cytoplasm. In contrast, over 90% of the control actin RNA was found in the cytoplasmic fraction (FIG. 13C).

Figure 14A:
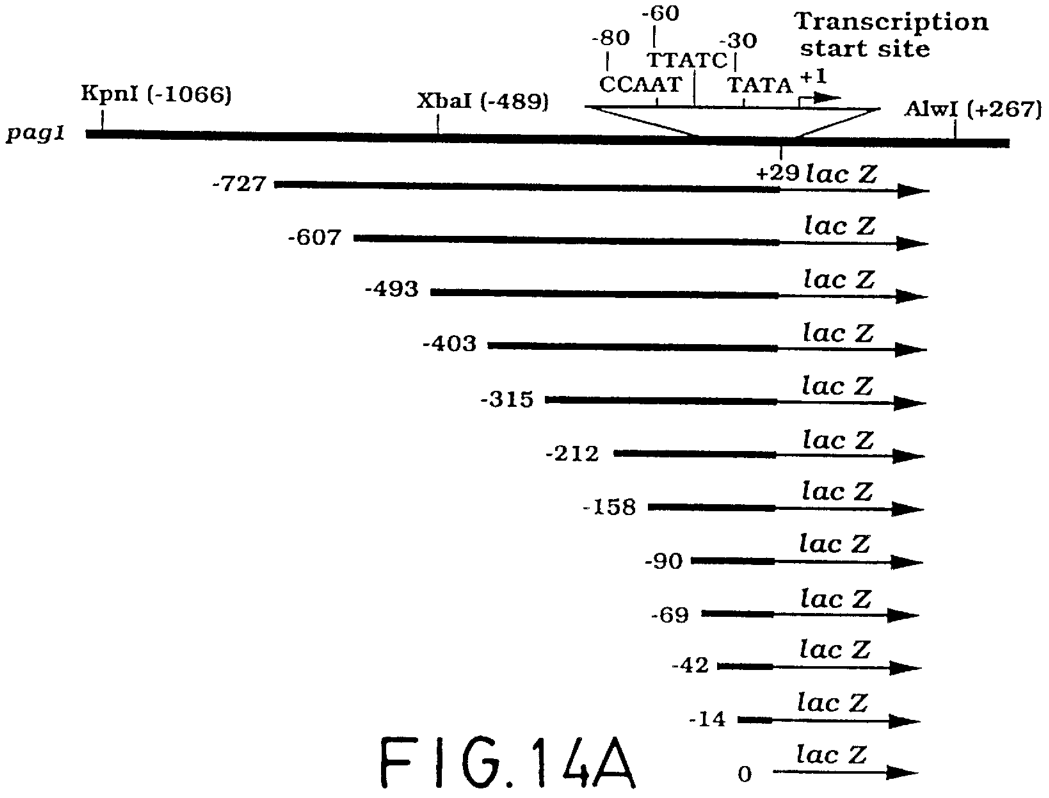
FIGS. 14A and 14B. Evidence showing that PAT1 is a genuine viral transcript rather than an intron remnant.
Figure 14B:
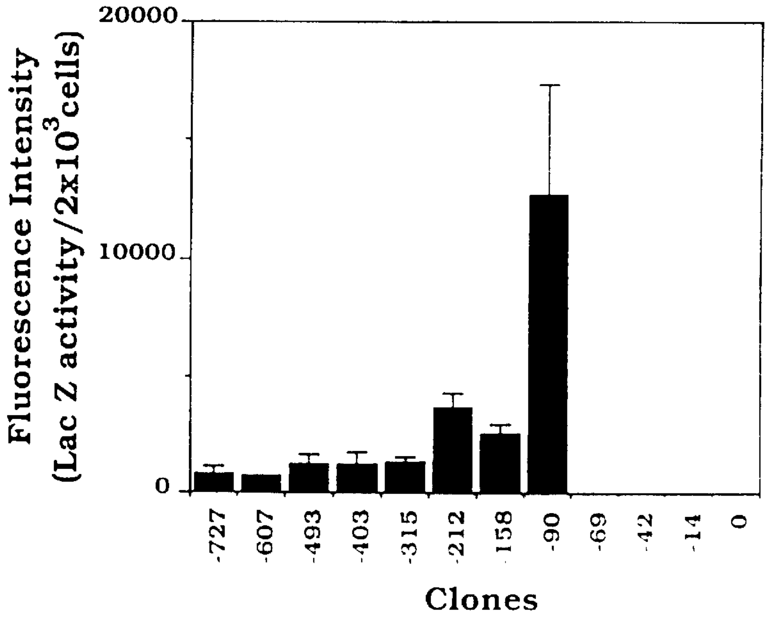

Unlike the promoter of LATs, the TATA box of the putative promoter of hem1 is located 24 bp upstream from the transcript start site of PAT1. To test whether the sequence adjacent to the transcriptional start site is the promoter, nested deletions in the putative PAT1 promoter region were constrcuted and transfected into SF9 cells. The intensity of downstream LacZ expression from individual deleted hem1 promoters was analysed to define the sequnce requirements for the promoter of hem1. Similar levels of promoter activity were observed when the promoter construct contained regions from nucleotide −727/29 to −315/29. The promoter activity increased when it was deleted up to nucleotide −212. Interestingly, when the construct was further deleted to the nucleotide −90 region, which contains putative CAAT and TATA boxes and a GATA motif, the strongest promoter activity was observed. Such unique expression patterns reveal complicated control mechanisms for expression of the hem1 promoter, by which a repressor and/or an activator may be utilized during productive and persistent viral infections. Further deletion into the nucleotide −90/+29 region abolished the promoter activity completely, indicating that the closely associated TATA box-containing region is crucial for PAT1 expression (FIG. 14). Therefore, PAT1 is unlikely to be an intron of other viral transcripts.

PAT1 is truly a unique viral transcript. It contains no significant ORFs and is not associated with ribosomes. In addition, it is located in the nucleus. All the aforementioned features of PAT1 are strikingly similar to those of Xist RNA found in female mammals. The cDNA sequences of Xist and a highly homologous transcript XIST contain no significant ORFs, and both transcripts are localized in the nucleus. All these transcripts, PAT1, Xist, and XIST are each expressed during massive gene shut-off in the viral genome or during inactivation of the mammalian X chromosome. Interestingly, direct tandem repeat clusters which are observed in the PAT1 coding region (data not shown) are also present in both the Xist and XIST sequences. These clustered repeats in Xist and XIST have been suggested to have functional significance in gene inactivation. The features and similarities between PAT1 and Xist are summarized in Table 2.

Comparison between PAT1 and Xist

| | PAT1 | Xist |
|---|---|---|
| Localization | nucleus | nucleus |
| Expression upon inactivation of the genome | yes | yes |
| Existence of significant ORF | no | no |
| Existence of clustered repeats | yes | yes |
| Size | 3kb | 15kb |

Both the Xist and XIST RNAs have been suggested to be responsible for X chromosome inactivation (N. Brockdorff et al. , *Cell*, 71:515–526, 1992; C. J. Brown et al., *Cell*, 71: 527–542, 1992; N. Brockdorff et al., *Nature*, 351: 329–331, 1991; C. J. Brown et al., *Nature*, 349:38–44, 1991). The common features shared by the Xist famaily and PAT1 indicate that repression of the genome by RNA molecules may not be limited to the X chromosome of female mammals, but may extend to viral genome inactivation during persistency/latency. In the herpes viruses, the relevant transcription activation factor, namely Vmw65 in HSV (Campbell et al., *J. Mol. Biol.*, 180:1–19, 1984; Steiner et al., *J. Virol.*, 64:1630–1638, 1990; S. P. Weinheimer, *J. Virol.*, 66:258–269, 1992) or BZLF1 (C. Rooney, *Proc. Natl. Acad. Sci. USA*, 85:9801–9805, 1988; E. Flemington and S. H. Speck, *J. Virol.*, 64:1227–1232, 1990; Sinclair et al., *J. Virol.*, 66:70–77, 1992) in Epstein-Barr virus, is the agent responsible for turning on the formatin of viral early transcripts and in turn ensures productive infection. Although it has been suggested in HSV that viral latent infection may be resulted passively from a lack of Vmw65, so far, very little is known about the mechanism for the establishment of viral latent infection in eukaryotic cells. The lack of such information makes the future study of possible viral genome inactivation by RNA, molecules especially attractive.

Thus far, detailed mutational analysis of the Xist genes is not yet available. The sizes of Xist and XIST (15 and 17 kb, respectively) are much greater than that of PAT1 (3 kb). In addition, PAT1 is expressed from a much smaller, easy-to-manipulate, 230-kb viral genome. The turning on and off of the viral productive-specific genes takes place in cell lines heres that of the Xist gene takes place in embryos (G. F. Ka Kay et al., *Cell*, 72:171–182, 1993). These unique features will give the Hz-1 baculovirus an advantage in future molecular analysis of the function of these novel nuclear RNAs.

From the above teachings, it is apparent that various modifications and variations can be made without departing from the spirit and scope of the present invention. It is therefore to be understood that this invention may be practiced otherwise than as specifically described.

I claim:

1. A method for inhibiting baculovirus superinfection in insect cells, comprising introducing a hem1 gene operatively linked to a promoter into an insect cell in vitro, wherein the insect cell is persistently infected with baculovirus, and wherein expression of the hem1 gene in the insect cells inhibits baculovirus superinfection by inducing cellular apoptosis.

2. The method of claim 1, wherein the hem1 gene is from Hz-1 baculovirus.

3. A method for inhibiting baculovirus infection in insect cells, comprising introducing a hem1 gene operatively linked to a promoter into an insect cell in vitro, wherein the hem1 gene is anti-viral gene, and wherein expression of the hem1 gene renders the insect cell resistant to baculovirus infection.

4. The method of claim 3, wherein the hem1 gene is from Hz-1 baculovirus.

* * * * *